US008907076B2

(12) United States Patent
Saxena et al.

(10) Patent No.: US 8,907,076 B2
(45) Date of Patent: Dec. 9, 2014

(54) MYCOBACTERIAL PEPTIDE DEFORMYLASE

(75) Inventors: Rahul Saxena, Chandigarh (IN); Pardip K. Chakraborti, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 12/835,293

(22) Filed: Jul. 13, 2010

(65) Prior Publication Data

US 2010/0273861 A1 Oct. 28, 2010

Related U.S. Application Data

(62) Division of application No. 11/888,610, filed on Aug. 1, 2007, now abandoned.

(30) Foreign Application Priority Data

Aug. 2, 2006 (IN) .......................... 1763/DEL/2006

(51) Int. Cl.
*C07H 21/04* (2006.01)
*C12N 15/113* (2010.01)
*C12N 9/80* (2006.01)

(52) U.S. Cl.
CPC ..... *C12N 15/1137* (2013.01); *C12Y 305/01088* (2013.01); *C12N 9/80* (2013.01); *C12N 2310/11* (2013.01)
USPC ........................................ 536/24.5; 536/24.1

(58) Field of Classification Search
None
See application file for complete search history.

(56) References Cited

PUBLICATIONS

Saxena et al. (J. Bactrol. 2005, pp. 8216-8220.*
Cole et al. NP-214943, 2002.*

* cited by examiner

*Primary Examiner* — Tekchand Saidha
*Assistant Examiner* — Md. Younus Meah
(74) *Attorney, Agent, or Firm* — Harness, Dickey & Pierce, PLC

(57) ABSTRACT

The present invention relates to the design of the Antisense-oligonucleotide complementary to the specific region of peptide deformylase gene from *Mycobacterium tuberculosis*. The use of this Antisense-oligonucleotide on mycobacterial culture inhibits the production of the peptide deformylase enzyme by hybridizing within the region, which is found to be responsible for maintaining stability as well as retaining the functionality of the enzyme and thus in turn affecting the growth of the cells. This invention also establishes the essentiality of the peptide deformylase enzyme in mycobacteria and claims it as a drug target in this microorganism.

18 Claims, 6 Drawing Sheets

(2 of 6 Drawing Sheet(s) Filed in Color)

```
E.coli         (SEQ ID NO: 22)      ----MSVLQVLHIPDERLRKVAKPVEEVN-----AEIQRIVDDMFETMY--------AEF
M.tuberculosis (SEQ ID NO: 22)          MAVVPIRIVGDPVLHTATTPVTVAADGSLPADLAQLIATMYDTMD        AAN
S.aureus       (SEQ ID NO: 22)      ---MLTMKDIIRDGHPTLRQKAAELELPLTKEEKETLIAMREFLVNSQDEEIAKRYGLRS
                                        ::: :    . *: : :             :  :   : ::            .

E.coli         (SEQ ID NO: 22)      GIGLAATQVDIHQRIIVIDVSENRDE----RLVLINPELLE------KSGETGIEEGCLS
M.tuberculosis (SEQ ID NO: 22)      GVGLAANQIGCSLRLFVYDCAADRAMTARRRGVVINPVLETSEIPETMDPDTDDEGCLS
S.aureus       (SEQ ID NO: 22)      GVGLAAPQINISKRMIAVLIPDDGSGKS-YDYMLVNPKIVSHS---VQEAYLPTGEGCLS
                                    ‾‾‾‾‾‾                                                 ‾‾‾‾‾
                                    Motif 1                   IR                          Motif 2
                                    *:**** *:.    *::.        . :        :::** :              *****

E.coli         (SEQ ID NO: 22)      IPE QRALVPRAEKVKIRALDRDGKPFELEADGLLAICIQHEMDHLVGKLFMDYLSPLKQ
M.tuberculosis (SEQ ID NO: 22)      VPG-ESFPTGRAKWARVTGLDADGSPVSIEGTGLFARMLQHETGHLDGFLYLDRLIGRYA
S.aureus       (SEQ ID NO: 22)      VDDNVAGLVHRHNRITIKAKDIEGNDIQLRLKGYPAIVFQHEIDHLNGVMFYDHIDKNHP
                                                                                  ‾‾‾‾‾‾‾
                                                                                  Motif 3
                                    :       . * :    :  . * :*.  ..:.  *   *  :***  .** * :: * :   .

E.coli         (SEQ ID NO: 22)      QRIRQKVEKLDRLKARA--------------
M.tuberculosis (SEQ ID NO: 22)      RNAKRAVKSHGWGVPGLSWLPGEDPDPFGH
S.aureus       (SEQ ID NO: 22)      LQPHTDAVEV---------------------
                                                  ‾‾‾‾‾‾‾‾‾‾‾‾‾‾‾‾‾
                                                  TR
                                    :  . .
```

FIG. 1

| M.tb     | MAVVPIRIVGDPVLHTATTPVTVAADGSLPADLAQLIATHYDTHDAANGVGLAANQIGCS |
| M.bovis  | MTVVPIRIVGDPVLHTATTPVTVAADGSLPADLAQLIATHYDTHDAANGVGLAANQIGCS |
| M.leprae | MAIAPIRIVGDPVLHTPTAPVQVAADGSLPANLNGLISTHYDTHDAAHGVGLAANQIGYG |
| M.avium  | MAVVPIRIVGDPVLHTPTQPVPVGDDGSLPADLGKLIADHYDTHDAAHGVGLAANQIGVG |
| M.smeg   | MAVVPIRIVGDPVLHTPTEPVPVGPDGSLPDDLPALIQDMFDTHDAANGVGLAANQIGVA |
|          | *:;,************,* ** *, ***** ;*  **   *;****;******** , |

| M.tb     | LRLFVYDCAADRANTAPRRGVVINPVLETSEIPETMPDPDTDDEGCLSVPGESFPTGRAK |
| M.bovis  | LRLFVYDCAADRANTAPRRGVVINPVLETSEIPETMPDPDTDDEGCLSVPGESFPTGRAK |
| M.leprae | LRVFVYDCAEDCRQTAPRRGVVINPILETSEIPETMPDPDTDNEGCLSVPGESFPIGRAQ |
| M.avium  | LRVFVYDCADDRGLTEPRRGVVVNPVLETSEIPETMPDPDTDDEGCLSVPGESFPTGRAS |
| M.smeg   | KRLFVYDCAPTRGQTTRRRGVVINPVLETSEVPETMPDPDEDEEGCLSVPGENFPTGRAD |
|          | *;******    *  ***;;***;****** *;*******, ***, |

| M.tb     | VARVTGLDADGSPVSIEGTGLFARMLQHETGHLDGFLYLDRLIGRYARNAKRAVKSHGVG |
| M.bovis  | VARVTGLDADGSPVSIEGTGLFARMLQHETGHLDGFLYLDRLIGRYARNAKRAVKSHGVG |
| M.leprae | VARVTGLDADGNPVTTEGTGLFARMLQHETGHLDGFLYLDYLIGRHARSAKRAIKSRHVG |
| M.avium  | VARVTGLDADGNPVSIEGHGLFARMLQHETGHLDGFLYLDRLIGRYARSAKRAVKSHNVG |
| M.smeg   | VARVTGLDADGSPITLEGEDLFARMLQHETGHLDGFLYLDRLVGRYARAAKKAVKRNGVG |
|          | **********,*;;  ,******************* *;; **;*;* , ** |

| M.tb     | VPGLSVLPGEDPDFGH |
| M.bovis  | VPGLSVLPGEDPDFGH |
| M.leprae | VPGLSVMPGEVPDFGP |
| M.avium  | VPGLSVMPGEPDPFGH |
| M.smeg   | VPGLSVMPGEVPDFGH |
|          | ****;* ***** |

FIG 2

MYCOBACTERIAL PEPTIDE DEFORMYLASE

CROSS-REFERENCE TO RELATED APPLICATIONS

This application is a Divisional of U.S. application Ser. No. 11/888,610, filed Aug. 1, 2007, now abandoned which claims the benefit of Application No. INDIA 1763/DEL/2006, filed Aug. 2, 2006, both of which are incorporated by reference in their entirety herein.

REFERENCE TO A SEQUENCE LISTING

The material in the ASCII text file entitled "Deformylase Sequence Listing.txt" is hereby incorporated by reference in its entirety. The ASCII text file entitled "Deformylase Sequence Listing.txt" was created on Jul. 17, 2012, and the size is 22,840 bytes.

FIELD

The present invention relates to identification of a specific region in the mycobacterial peptide deformylase enzyme useful as a potential drug target against Mycobacteria.

The present invention further relates to the design of an antisense oligonucleotide complementary to the specific region of peptide deformylase gene from Mycobacterium tuberculosis. The use of this antisense oligonucleotide on mycobacterial culture inhibits the production of the peptide deformylase enzyme by hybridizing within the region, which is found to be responsible for maintaining stability as well as retaining the functionality of the enzyme and thus in turn affecting the growth of the cells. This invention also establishes the essentiality of the peptide deformylase enzyme in mycobacteria and claims it as a drug target in this microorganism.

BACKGROUND

The statements in this section merely provide background information related to the present disclosure and may not constitute prior art.

In the past, few decades' tuberculosis has emerged as a cause of considerable human mortality worldwide. It has been found that there is a steady increase in the frequency of mycobacterial strains, which have developed resistance against one or more anti-mycobacterial agents commonly used in treatment. Therefore, to overcome the situation there is a need to have better drug intervention strategies, which can be achieved by identification of new drug targets. In this consequence, the enzyme peptide deformylase is involved in deformylation of nascent polypeptides, which appears to be a mandatory step in mycobacterial protein synthesis in general. Therefore, any biotic/abiotic factor(s) inhibiting this enzyme may prevent protein synthesis in general in mycobacteria and thus specifically inhibits its growth.

Drug resistance in pathogenic microorganisms has emerged as a great threat to public health worldwide. Although there is large number of antibiotics used, the variety of target they inhibit is very limited. Consequences of the prolonged and excessive use of these antibiotics outlay multidrug resistance in the pathogenic microorganisms. Therefore, in order to diversify the spectrum of antimicrobial agents, there is an urgent need to frame new intervention strategies, based on rational approaches, which would allow improved drug design.

Protein synthesis has always been proven to be a rich source of targets for antimicrobials. In contrast to the eukaryotes, protein synthesis in prokaryotes is initiated with N-formyl-methionyl-tRNA leading to formylation of all nascent polypeptides at the amino-terminal end. The N-formylmethionine, however, is not retained in mature proteins of eubacteria and has been reported to be deformylated by peptide deformylase. This formylation/deformylation event appears to be a mandatory step in eubacterial protein synthesis and therefore, the importance of this enzyme has long been envisaged.

Available genome sequencing data revealed the presence of putative gene encoding the peptide deformylase (def) throughout the eubacterial lineage including pathogens like Mycobacterium tuberculosis (NCBI general identification GI: 38490165; SEQ ID NO: 8), Staphylococcus aureus, (NCBI general identification GI: 57651784 SEQ ID NO: 1) Streptococcus pneumoniae (NCBI general identification GI: 16272565 SEQ ID NO: 2), Haemophillus influenzae (NCBI general identification GI: 16272565; SEQ ID NO: 3), Leptospira interrogans (NCBI general identification GI: 14626937; SEQ ID NO: 4), Enterococcus feacelis (NCBI general identification GI: 29377524; SEQ ID NO: 5), Helicobacter pyroli (NCBI general identification GI: 49089809; SEQ ID NO: 6) and Bacillus subtilis (NCBI general identification GI: 16078635; SEQ ID NO: 7). etc. Earlier studies have shown the identification and use of various compounds or preparations and their derivative inhibiting the activity of peptide deformylase in various microorganisms (Patent no: WO0138561, WO2005026133, WO2005037272, WO2005092872 etc).

The article by Tomioka, H (Prospects for development of new antituberculous drugs. Kekkaku. August; 77[8] 573-84, 2002) in general describes the pharmacological status of certain new derivatives of existing drugs such as rifamycin (rifabutin, rifapentine, and rifalazil), fluoroquinolones (ciprofloxacin, ofloxacin, sparfloxacin, levofloxacin, gatifloxacin, sitafloxacin, moxifloxacin, and others), and new macrolides (clarithromycin, azithromycin, and roxithromycin). This review also discusses the importance of the development of new antimycobacterial, especially antituberculous agents including oxazolidinone (PNU-100480), 5'-nitroimidazole (CGI 17341), 2-pyridone (ABT-255), new riminophenazines, nitroimidazopyran (PA-824), new ketolides (ABT-773, telithromycin) and defensins (human neutrophil peptide-I). Moreover, authors have described the possibility of designing inhibitors (certainly one of the strategy could be an antisense technology) specific to mycobacterial genes encoding certain metabolic enzymes or virulence factors as a new drug targets. In fact, use of antisense oligonucleotides to shut down the expression of mycobacterial genes is a very familiar technique (For reference: Harth at al., Proc. Natl. Acad. Sci. U.S.A. 99, 15614-15619, 2002).

The present invention highlights the importance of Insertion sequence specifically present in mycobacterial peptide deformylase (consisting of amino acids 74-85, (Please refer FIG. 1 and FIG. 2) responsible for maintaining the functionality of the enzyme (FIG. 5, where it is shown that deletion mutant of this region did not show any enzyme activity). Furthermore, the use of antisense oligonucleotide (complementary to the corresponding nucleic acid of SEQ ID NO: 21) against the insertion region reduces the expression of peptide deformylase enzyme (as shown in FIG. 8 by western blotting using anti-mPDF antibody), which in turn leads to the growth inhibition of mycobacteria in culture (FIG. 6A and left panel of FIG. 7). These results therefore describe the novelty of the insertion region of mycobacterial enzyme, which we have invented, in terms of the possibility of designing inhibitors based on this insertion region (Antisense molecule has been used to elucidate the importance of the region in contributing mycobacterial growth).

In another article by Cynamon, et al. 2004. Journal of Antimicrobial Chemotherapy. 53: 403-405 it is recited that actinonin an antibiotic isolated from class Actinomycetes as well as BB3497 (a hydroxamic acid derivative of actinonin) showed inhibition for PDF enzyme activity from different microorganisms by binding to the active site. The mentioned article describes the inhibitory effect of BB3497 on the growth of mycobacteria in culture possibly by inhibiting PDF enzyme activity. Cynamon, et al. 2004 in their paper showed a known peptide deformylase inhibitor inhibits mycobacterial growth. On the other hand, we initiated our studies through characterization of mPDF and established that despite the commonality, it is distinctly different from other bacterial homologues. Sequence analysis of peptide deformylase of *M. tuberculosis* revealed the presence of characteristic insertions (residues 74-85) between motifs I and II (FIG. 1). The result of the instant application with deletion mutant indicates the contribution of this region towards functionality of the enzyme (FIG. 5). Among PDFs characterized to-date, our analysis revealed that the constituent amino acids of the insertion region is typical of mycobacterial species (FIG. 2). Moreover, using 5'-phosphothiorate-modified antisense oligodeoxyribonucleotides directed against this insertion region, we showed inhibition of mycobacterial growth in cultures, establishing the importance of this region (FIG. 6A). Furthermore, antisense oligonucleotide directed against insertion sequence specific to mycobacteria has no effect on the functionality of PDF enzyme from other bacteria such as *Escherchia coli* (as shown in right panel of FIG. 7). Thus our results clearly establish that the antisense oligonucleotide directed against the insertion region specifically inhibits the expression of the mycobacterial peptide deformylase enzyme (FIG. 8) and therefore, the growth of the mycobacteria (FIG. 6A and left panel of FIG. 7). Hence, we claim that we have identified a region in mycobacterial peptide deformylase enzyme (amino acid residues 74-85), which is important towards the functionality of the enzyme in mycobacteria. Any molecule (biotic or abiotic) that interacts with this region of the mycobacterial enzyme and affects the expression or production of this enzyme can inhibit mycobacterial growth. (We established this by using an antisense oligonucleotide directed against this region. So it is an approach to validate our conclusion/invention). Therefore, this region (amino acid residues 74-85), which we have identified in mycobacteria for the first time as well as established its importance (FIGS. 5 to 8) is definitely a drug target for development of antimycobacterials.

Huntington, K. M. 2000. Biochemistry. April 18; 39[15]; 4543-51 reports the recent information on the whole genome of various pathogenic bacteria including *M. tuberculosis* certainly provides a good platform to promote the progression in the identification of genes that code for new drug targets. Essential genes encoding proteins involved in metabolism and survival of pathogenic microorganisms are always being preferential vaccine candidates. Similarly, peptide deformylase is among one of the essential enzyme, which is involved in posttranslational modification of N-formylated polypeptides in prokaryotes (Mazel et al., 1994, Margolis et al., 2000 and 2001). It has been characterized as either zinc or ferrous containing metalloprotease in many eubacteria. Its essential character in bacterial cells makes it an attractive target for antibacterial drug design. Authors in the above mentioned article showed that they have rationally designed and synthesized a series of peptide thiols that act as potent, reversible inhibitors of purified recombinant peptide deformylase from *Escherichia coil* and *Bacillus subtilis* by binding to the active site. The PDF inhibitors induce bacterial cell lysis and have been tested to be bactericidal to *B. subtilis, Staphylococcus epidermidis, Enterococcus faecalis*, and *E. coli*. However, the present invention is specifically focused to *M. tuberculosis*. Authors have nowhere mentioned the effect of these compounds on the activity of purified mycobacterial enzyme as well as on the growth of mycobacteria. On the other hand, our work specifically deals with mycobacterial PDF and claims for the first time that an insertion sequence specific to mycobacterial enzyme could be focused to develop new antimycobacterials.

Recently, we have PCR amplified the 594 base pair def gene from *M. tuberculosis* and following cloning in pET28c vector, expressed it as a histidine-tagged fusion protein in *Escherichia coli* (Saxena and Chakraborti, Biochem Biophys Res Commun (332): 418-425, (2005)). Although atomic absorption spectroscopy revealed that mPDF was a $Fe^{+2}$-containing enzyme, its activity was very stable at 30° C. with a half-life of ~4 h. Furthermore, it maintained its distinction by exhibiting resistance to oxidizing agents, like $H_2O_2$ (Saxena and Chakraborti, Biochem Biophys Res Commun 332: 418-425, 2005); Saxena and Chakraborti, J. Bacteriol 187: 8216-8220 2005). Since conversion of $Fe^{+2}$ to $Fe^{+3}$ by environmental oxygen resulted in inactivation of this metalloprotease in *E. coil* (Rajagopalan, et. al., J. Biol. Chem 36: 13910-13918, 1997), this seems to be an important observation considering the fact that *M. tuberculosis* has to cope up with oxidative stress for its survival within the host as a successful pathogen.

This led us to characterize the mycobacterial peptide deformylase enzyme. In contrast to other studies (Patent no. WO02074903), our invention is related to use of an antisense oligonucleotide complementary to specific nucleotide region of the mycobacterial peptide deformylase gene (def), which inhibits enzyme activity, as well as the growth of this microorganism in culture establishing its essentiality and its potential as a drug target.

OBJECTS OF THE INVENTION

The main object of the invention is to provide the mycobacterial peptide deformylase [def] gene sequence, represented by SEQ ID NO: 21.

Another object of the invention is thus to provide the amino acid sequence 74 to 85 corresponding to SEQ ID NO: 13 of the def gene of *Mycobacteria*, useful as a potential drug target against *Mycobacteria*.

Another object of the present invention is to provide an antisense oligonucleotide against Mycobacterial Peptide deformylase.

Yet another object of the present invention is to provide an oligonucleotide useful for inhibiting the activity and growth of *Mycobacteria*.

Still another object of the present invention is to provide a modified antisense oligonucleotide against Mycobacterial Peptide Deformylase.

A further object of the invention is to provide a process for the preparation of said antisense oligonucleotide.

Yet another objective of the invention is to provide a pharmaceutical composition useful for the treatment of tuberculosis comprising an oligonucleotide, optionally along with pharmaceutically acceptable carriers, additives or diluents.

Advantages:

In the past few decades, tuberculosis has re-emerged as a global health hazard causing millions of deaths worldwide. Although there are several anti-tuberculosis drugs are known, the emergence of single or multidrug resistant strains of pathogenic mycobacterial species has widely been regarded as one of the prime causes for the resurgence of this dreadful disease. To overcome the situation there is an urgent need to develop novel drug intervention strategies. To achieve this objective, identification of drug target is a prime requirement. In this context, the present invention is focused on protein synthesis in mycobacteria in general, which has always been proven to be a rich source of targets for screening of antibacterial compounds. In contrast to synthesis of cytosolic proteins in eukaryotes, the formylation/deformylation event appears to be a mandatory step in eubacteria and therefore, the importance of PDF enzyme has long been envisaged. Despite commonality with different bacterial PDFs, the mycobacterial PDF has several distinctive features. Among them, the contribution of insertion (residues 74-85) sequences (specific to mycobacterial species only) in maintaining the enzymatic stability as well as functionality of this protein is the significant feature, which has not been reported to-date from any other bacteria. The phosphothiorate modified antisense oligonucleotide designed and synthesized against the insertion sequence hampered mycobacterial growth in culture as well as expression of the mycobacterial peptide deformylase enzyme. Thus, these results highlighted the novelty of the insertion region of mycobacterial enzyme based on which rational drug designing is possible. Hence, this invention will definitely be advantageous in identifying/developing of any antimycobacterial compound (biotic or abiotic) that interacts with this region of the mycobacterial enzyme as well as affects the expression or production of this enzyme can inhibit mycobacterial growth.

SUMMARY

Accordingly, the present invention provides an antisense oligonucleotide (SEQ ID NO: 14) complementary to the mycobacterial peptide deformylase [def] gene sequence, represented by SEQ ID NO: 21, which correspond to 12 amino acids represented by XTXRRRGVVINP (SEQ ID NO: 13), wherein X is any one of the 20 known amino acids. The present invention is further related to the use of antisense-oligonucleotide (SEQ ID NO: 14) on mycobacterial culture for inhibiting the production of the peptide deformylase enzyme by hybridizing within this region and thus in turn affecting the growth of the mycobacterial cells. The region (amino acid sequence 74 to 85) within the peptide deformylase enzyme from M. tuberculosis is found to be involved in maintaining the enzymatic stability as well as retaining the functionality of the mycobacterial enzyme and thus highlighting its importance. The prevention of growth of mycobacterial cells in culture treated with the said oligonucleotide further establishes the essentiality of the peptide deformylase enzyme in mycobacteria and therefore, claims it as a drug target in this microorganism. The invention further provides the mycobacterial peptide deformylase [def] sequence comprising 12 amino acids represented by XTXRRRGVVINP SEQ ID NO: 13, wherein X=any one of the 20 known amino acids, is 90 to 95% similar in M. tuberculosis, M. smegmatis, M. bovis, M. avium and M. leprae. The said amino acid sequence of the def gene of Mycobacteria is a potential drug target against Mycobacteria.

In one embodiment of the present invention, the mycobacterial peptide deformylase [def] gene sequence is represented by SEQ ID NO: 21.

In another embodiment of the present invention, the said sequence is useful as a potential drug target against Mycobacteria.

In yet another embodiment of the present invention, SEQ ID NO: 13 comprises 12 amino acids represented by XTXRRRGVVINP, wherein X=any one of the 20 known amino acids.

In a further embodiment of the present invention, the amino acid sequence is 90 to 95% similar in M. tuberculosis, M. smegmatis, M. bovis, M. avium and M. leprae.

In another embodiment of the present invention is an antisense oligonucleotide (SEQ ID NO: 14) complementary to the gene sequence represented by SEQ ID NO: 21.

In a further embodiment of the present invention, the oligonucleotide is characterized in that it is either a single (5') or throughout phosphorothioate modified oligodeoxynucleotide.

In yet another embodiment of the present invention, the said oligonucleotide inhibits the production of the enzyme peptide deformylase by hybridizing within the short region of mycobacterial peptide deformylase (def) gene.

In another embodiment of the present invention, the said oligonucleotide is a potential drug against Mycobacteria In yet another embodiment of the present invention is a process for the preparation of an antisense oligonucleotide (SEQ ID NO: 14), the said process comprising the steps of isolating polynucleotide sequence from M. tuberculosis comprising nucleic acid sequence (594 bp) encoding a polypeptide (197 amino acids) having peptide deformylase activity wherein, the polypeptide is present in different mycobacterial species like M. tuberculosis, M. smegmatis, M. bovis, M. avium, M. leprae represented by SEQ ID NO: 8, 9, 10, 11, 12 and having at least 90 to 95%, sequence similarity among themselves; identifying a region within mycobacterial peptide deformylase enzyme isolated from step (a) represented by polynucleotide SEQ ID NO: 21 and amino acid sequences 74 to 85 involved in maintaining the enzymatic stability and functionality, the said region being conserved in all of the mycobacterial species; preparing an antisense oligonucleotide (SEQ ID NO: 14) or its permissive modifications, against the conserved region of peptide deformylase enzyme; inhibiting the enzyme activity as well as growth of the mycobacteria using the antisense oligonucleotide.

In a further embodiment of the present invention is the use of the polynucleotide sequence as a potential drug target against Mycobacteria.

In yet another embodiment of the present invention is the use of the amino acid sequence of the def gene of Mycobacteria as a potential drug target against Mycobacteria.

In another embodiment of the present invention is the use of the oligonucleotide (SEQ ID NO: 14) for inhibiting the activity and growth of Mycobacteria.

In a further embodiment of the present invention is provided a pharmaceutical composition, comprising an oligonucleotide optionally along with pharmaceutically acceptable carriers, additives or diluents, the said composition being useful for the treatment of tuberculosis.

Further areas of applicability will become apparent from the description provided herein. It should be understood that the description and specific examples are intended for purposes of illustration only and are not intended to limit the scope of the present disclosure.

DRAWINGS

The file of this patent contains at least one drawing executed in color. Copies of this patent with color drawings will be provided by the Patent and Trademark Office upon request and payment of necessary fee.

The drawings described herein are for illustration purposes only and are not intended to limit the scope of the present disclosure in any way.

FIG. 1 is a sequence alignment of *M. tuberculosis* enzyme with that of other bacterial iron-containing peptide deormylases;

FIG. 2 is a multiple sequence alignment of peptide deformylase enzyme from different mycobacterial species;

DETAILED DESCRIPTION

Figure 3:
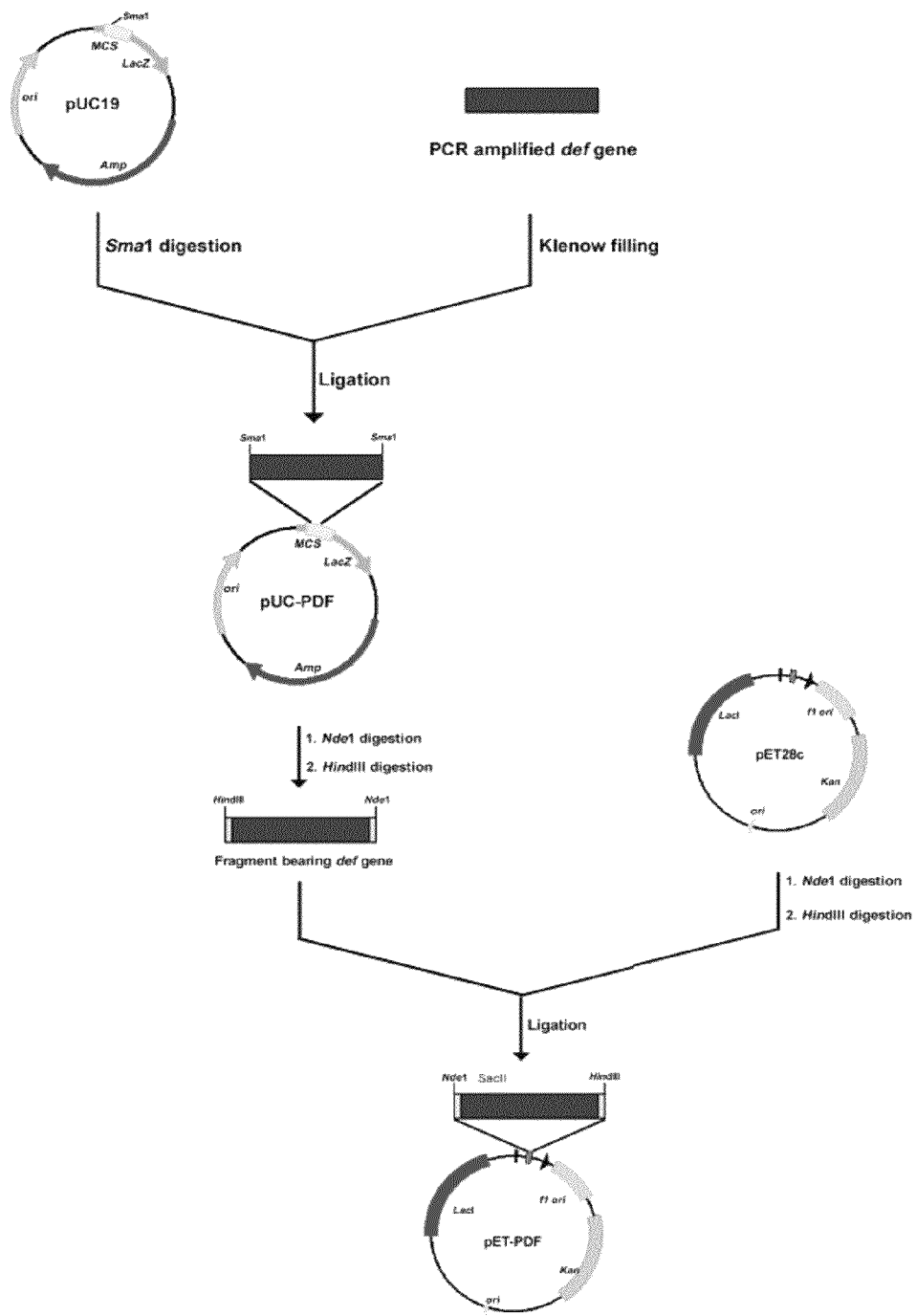
FIG. 3 is schematic representation of cloning of mycobacterial peptide deformylase gene in expression vector.
Figure 4:
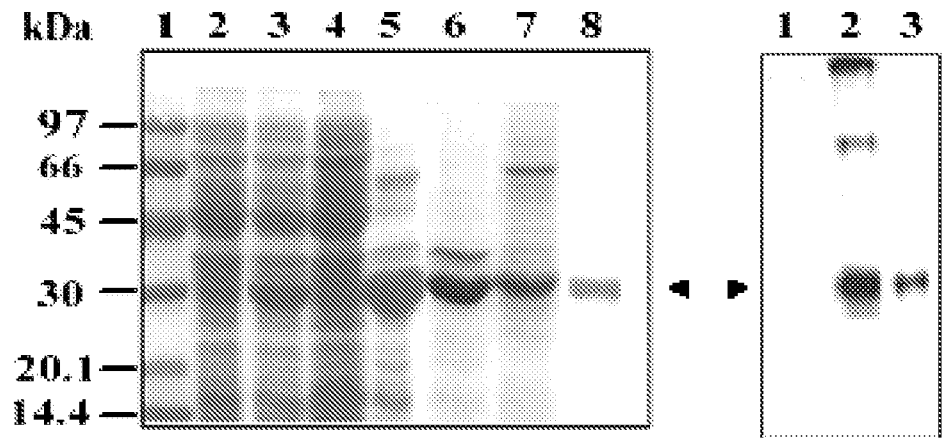
FIG. 4 depicts a purification of peptide deformylase of *M. tuberculosis* expressed in *E. coli*.

The following description is merely exemplary in nature and is not intended to limit the present disclosure, application, or uses.

The present invention deals with peptide deformylase from pathogenic bacterium *M. tuberculosis* causing dreadful disease tuberculosis. The present invention is related to the designing of the antisense-oligonucleotide (SEQ ID NO: 14) complementary to the specific region of peptide deformylase from *Mycobacterium tuberculosis*. The region within the peptide deformylase enzyme from *M. tuberculosis* is involved in maintaining the enzymatic stability as well as retaining the functionality of mycobacterial enzyme. The use of antisense-oligonucleotide (SEQ ID NO: 14) on mycobacterial culture inhibits the production of the peptide deformylase enzyme by hybridizing within this region and thus in turn affecting the growth of the mycobacterial cells.

In the context of this disclosure, a number of terms shall be utilized. The terms "polynucleotide sequence", "nucleic acid sequence", "nucleic acid fragment", "isolated polynucleotide sequence", "polypeptide", and "polypeptide sequence" are used interchangeably herein. These terms encompass nucleotide/amino acid sequences and the like. A polynucleotide may be a polymer of RNA or DNA, which is either single- or double-stranded. Similarly, polypeptide is a polymer of 20 different amino acids arranged in various fashions to translate for a functional protein. A polynucleotide in the form of a polymer of DNA may be comprised of a sequence of genomic DNA or synthetic DNA.

As used herein "Gene" refers to a nucleic acid fragment that expresses a specific protein.

A "protein" or "polypeptide" is a chain of amino acids arranged in a specific order determined by the coding sequence in a polynucleotide encoding the polypeptide. Each protein or polypeptide has a unique function.

"Mature protein" or the term "mature" when used in describing a protein refers to a post-translationally processed polypeptide.

As used herein, the term "region" refers to the short conserved sequences of nucleic acids or amino acids that comprise part of a longer sequence and is expected that such conserved subsequences would be important for function, and could be used to identify new targets. It is expected that one or two of the conserved amino acids in any given conserved sequence may differ in a true homologue.

As used herein, "substantially similar" refers to nucleic acid fragments wherein changes in one or more nucleotide bases results in substitution of one or more amino acids, but do not affect the functional properties of the polypeptide encoded by the nucleotide sequence.

"Substantially similar" also refers to nucleic acid fragments wherein changes in one or more nucleotide bases does not affect the ability of the nucleic acid fragment to mediate alteration of gene expression by gene silencing through for example antisense technology.

An Antisense oligodeoxynucleotide (SEQ ID NO: 14) used in the present study, designed on the basis of specific sequence of *M. tuberculosis* inhibits the growth of *M. smegmatis* without sharing 100% sequence identity in between two sequences. Moreover, substantially similar nucleic acid fragments may also be characterized by their ability to hybridize. Estimates of such homology are provided by either DNA-DNA or DNA-RNA hybridization under conditions of stringency.

Furthermore, "substantial portion" of an amino acid or nucleotide sequence comprises an amino acid or a nucleotide sequence that is sufficient to afford putative identification of the protein or gene that the amino acid or nucleotide sequence comprises.

As used herein, "growth inhibition" is related in terms of difference in colony forming unit and growth curves of Antisense-oligonucleotides treated and untreated microorganism.

"PCR" or "polymerase chain reaction" is well known technique used for the amplification of specific DNA segments (U.S. Pat. Nos. 4,683,195 and 4,800,159).

| SEQ ID NO | Strain | Molecule | Comment | Sequence |
|---|---|---|---|---|
| 1 | *Staphylococcus aureus* | Protein | *Staphylococcus aureus* polypeptide deformylase (NCBI general identification GI: 57651784 | Maikklvpas hpiltkkaqa vktfddslkr llqdledtmy aqeaaglcap qinqslqvai idmemegllq lvnpkiisqs netitdlegs itlpdvygev trskmivves ydvngnkvel tahedvarmi lhiidqmngi pfteradril tdkeveayfi nd |
| 2 | *Streptococcus pneumoniae* | Protein | *Streptococcus pneumoniae* polypeptide deformylase (NCBI general | msaieritka ahlidmndii regnptlrtv aeevtfplsd qeiilgekmm qflkhsqdpv maekmglrgg vglaapqldi skriiavlvp niveegetpq eaydleaimy npkivshsvq daalgegegc lsvdrnvpgy vvrharvtvd |

| SEQ ID NO | Strain | Molecule | Comment | Sequence |
|---|---|---|---|---|
| | | | identification GI: 15858846 | yfdkdgekhr iklkgynsiv vqheidhing imfydrinek dpfavkdgll ile |
| 3 | Haemophillus influenzae | Protein | Haemophillus influenzae polypeptide deformylase (NCBI general identification GI: 16272565 | mtalnvliyp ddhlkvvcep vtkvndairk ivddmfdtmy qekgiglaap qvdilqriit idvegdkqnq fvlinpeila segetgieeg clsipgfral vprkekvtvr aldrdgkeft ldadgllaic iqheidhlng ilfvdylspl krqrikekli kykkqiaks |
| 4 | Leptospira interrogans | Protein | Leptospira interrogans polypeptide deformylase (NCBI general identification GI: 14626937 | msvrkilrmg dpilrkisep vtedeiqtke fkklirdmfd tmrhaegvgl aapqigilkq ivvvgsedne rypgtpdvpe riilnpvitp ltkdtsgfwe gclsvpgmrg yverpnqirm qwmdekgnqf detidgykai vyqhecdhlq gilyvdrlkd tklfgfnetl dsshnvld |
| 5 | Enterococcus feacelis | Protein | Enterococcus feacelis polypeptide deformylase (NCBI general identification GI: 29377524 | mitmkdiire gnptlravae evpvpiteed rqlgedmltf lknsqdpvka eelqlrggvg laapqldisk riiavhvpsn dpenetpsls tvmynpkils hsvqdvclge gegclsvdrd vpgyvvrhnk itvsyfdmag ekhkvrlkny eaivvqheid hingimfydh inkenpfalk egvlvie |
| 6 | Helicobacter pylori | Protein | Helicobacter pylori polypeptide deformylase (NCBI general identification GI: 49089809 | malleiihyp skilrtiske vvsfdaklhq qlddmyetmi asegiglaai qvglplrmli inlpqedgvq hkedcleiin pkfietggsm mykegclsvp gfyeeverfe kvkieyqnrf aevkvlease llavaiqhei dhlngvlfvd klsilkrkkf ekelkelqkk qkhk |
| 7 | Bacillus subtilis | Protein | Bacillus subtilis polypeptide deformylase (NCBI general identification GI: 16078635) | mavkkvvthp aevletpaet vtvfdkklkk llddmydtml emdgvglaap qigilkraav veigddrgri dlvnpeilek sgeqtgiegc lsfpnvygdv tradyvkvra fnrqgkpfil eargflarav qhemdhldgv lftskiskyy tedeladmeg |
| 8 | Mycobacteria tuberculosis | Protein | Mycobacterium tuberculosis polypeptide deformylase (NCBI general identification GI: 38490165 | MAVVPIRIVGDPVLHTATTPVTVAADGSLPADLA QLIATMYDTMDAANGVGLAANQIGCSLRLFVYDC AADRAMTARRRGVVINPVLETSEIPETMPDPDTD DEGCLSVPGESFPTGRAKWARVTGLDADGSPVSI EGTGLFARMLQHETGHLDGFLYDRLIGRYARNA KRAVKSHGWGVPGLSWLPGEDPDPFGH |
| 9 | Mycobacterium smegmatis | Protein | Mycobacterium smegmatis polypeptide deformylase (MSMEG0826 peptide deformylase (def) [3.5.1.88 | MAVVPIRIVGDPVLHTPTEPVPVGPDGSLPDDLP ALIQDMFDTMDAANGVGLAANQIGVAKRLFVYDC APTRGQTTRRRGVVINPVLETSEVPETMPDPDED EEGCLSVPGENFPTGRADWARVTGLDADGSPITL EGEDLFARMLQHETGHLDGFLYDRLVGRYARAA KKAVKRNGWGGVPGLSWMPGEVPDPFGH |
| 10 | Mycobacterium bovis | Protein | Mycobacterium bovis polypeptide deformylase (NCBI general identification GI: 31617046 | MTVVPIRIVGDPVLHTATTPVTVAADGSLPADLA QLIATMYDTMDAANGVGLAANQIGCSLRLFVYDC AADRAMTARRRGVVINPVLETSEIPETMPDPDTD DEGCLSVPGESFPTGRAKWARVTGLDADGSPVSI EGTGLFARMLQHETGHLDGFLYDRLIGRYARNA KRAVKSHGWGVPGLSWLPGEDPDPFGH |
| 11 | Mycobacterium avium | Protein | Mycobacterium avium polypeptide deformylase (NCBI general identification GI: 41398721 | MAVVPIRIVGDPVLHTPTQPVPVGDDGSLPADLG KLIADMYDTMDAAHGVGLAANQIGVGLRVFVYDC ADDRGLTERRRGVVVNPVLETSEIPETMPDPDTD DEGCLSVPGESFPTGRASWARVTGLDADGNPVSI EGHGLFARMLQHETGHLDGFLYDRLIGRYARSA KRAVKSHNWGVPGLSWMPGEGPDPFGH |
| 12 | Mycobacterium leprae | Protein | Mycobacterium leprae polypeptide deformylase (NCBI general | MAIAPIRIVGDPVLHTPTAPVQVAADGSLPANLN GLISTMYDTMDAAHGVGLAANQIGYGLRVFVYDC AEDCRQTARRRGVVINPILETSEIPETMPDPDTD NEGCLSVPGESFPIGRAQWARVTGLDADGNPVTT |

| SEQ ID NO | Strain | Molecule | Comment | Sequence |
|---|---|---|---|---|
| | | | identification GI: 13093428 | EGTGLFARMLQHETGHLDGFLYLDYLIGRHARSA KRAIKSRHWGVPGLSWMPGEVPDPFGP |
| 13 | Mycobacterial | Protein | Mycobacterial peptide deformylase insertion sequence | XTXRRRGVVINP |
| 14 | Mycobacterium tuberculosis | DNA | Mycobacterial peptide deformylase gene antisense oligonucleotide | CGATT GATGACCACA CCGCGTCGGC GGGCGGTCAT |
| 15 | | DNA | CR1 Primer | CATATGGCAGTGGTACCC |
| 16 | | DNA | CR3 Primer | CCATTAGTGACCGAACGGG |
| 17 | | DNA | CR26 Primer | GGAATTCCATATGGCAGTCGTACCC |
| 18 | | DNA | CR27 Primer | CCCAA GCTT TTAGTGACCGAACGG |
| 19 | | DNA | CR87 Primer | GAGGTCTCAAGCACTGCGCGGTCCG |
| 20 | | DNA | CR88 Primer | GCGGACCGCGCA GTG CTTGAGACCTC |
| 21 | | DNA | Sense oligonucleotide to SEQ ID NO: 14 | ATGACCGCCC GCCGACGCGG TGTGGTCATC AATCCG |

Characterization of peptide deformylase open reading frame from *Mycobacterium tuberculosis* (mPDF):

Genomic DNA was isolated from *M. tuberculosis* strain H37Ra and used for PCR amplification of mPDF gene (def). Primers (CR1: 5" CATATGGCAGTGGTACCC 3" (SEQ ID NO: 15) where NdeI site was incorporated and CR3: 5" CCATTAGTGACCGAACGGG 3" (SEQ ID NO: 16)) used were designed based on def (Rv0429c) sequence of published *M. tuberculosis* genome (Cole et al., Nature. 393 537-544 (1998)). The def open reading frame (594 bp) was PCR amplified using Expand long template PCR system (Roche, Germany) following manufacturer's recommended protocol. Following treatment with DNA polymerase I (Klenow), the PCR-amplified fragment was initially cloned in pUC19 vector (pUC-PDF; FIG. 3) and its nucleic acid sequence was determined using an automated sequencer. The construct was subsequently used for subcloning of def open reading frame at NdeI/HindIII sites of pET28c and transformed in *E. coli* strain DH5α (pET-PDF; FIG. 3). Clones containing gene of interest were confirmed by restriction analysis.

The pET-PDF was transformed into *E. coli* strain BL21 (DE3) for over-expression. For purification of proteins, overnight culture of these colonies (~15 h at 37° C. in LB broth containing 50 μg/ml of kanamycin) were re-inoculated and grown until $OD_{600}$ of ~0.8. Cells were then induced with 0.4 mM IPTG at 25° C., harvested after 12 h and suspended in lysis buffer (20 mM phosphate buffer, pH 7.4 containing 5 mM DTT, 10 μg/ml of catalase, 1 mM phenylmethylsulfonyl fluoride, 1 μg/ml of pepstatin and 1 μg/ml of leupeptin). Cells were sonicated and the pellet fraction (~12,000×g for 30 min at 4° C.) was resuspended in lysis buffer containing 3M urea and 2% Triton X100. Following centrifugation, supernatant fraction was dialyzed (14 h at 4° C.) to remove urea and purified on Ni-NTA column (Qiagen) following manufacturer's recommended protocol. Finally, mPDF was eluted in elution buffer (20 mM phosphate buffer, pH 7.4 containing 300 mM NaCl, 250 mM imidazole and 10 μg/ml of catalase) and protein concentration was estimated following Bradford's method (Bradford M. M, Anal. Biochem. 72 248-254 1976).

The mPDF protein at different stages of purification was run in 12% SDS-PAGE and its identity was confirmed by Western blotting using anti-histidine antibody (FIG. 4). The protein concentration of the purified mPDF stock was maintained at 3.5 mg/ml and stored at −80° C. until used. mPDF was diluted in dilution buffer (20 mM phosphate buffer, pH 7.4 containing 1 mg/ml of BSA and 10 μg/ml of catalase) adjusting protein concentration at 3.5 μg/ml prior to use in assays. Atomic absorption spectroscopy was carried out by injecting 30 μg of mPDF sample (prepared in 20 mM phosphate buffer, pH 7.4) to graphite furnace. Iron content present in mPDF was calculated using standard curve prepared using 1-10 μg of $FeSO_4$. It revealed presence of iron at the catalytic core (0.94±0.21 mol of iron/mol of mPDF polypeptide, n=4).

The ability of mPDF to deformylate methionine was assessed in a spectrophotometric assay following the method described by Groche et al (Groche et al., Biochem. Biophys. Res. Commun. 246 342-346 1998) with slight modification. The assay was carried out in 50 μl reaction volume mPDF protein (usually 70 ng) in 1× assay buffer (100 mM phosphate buffer, pH 7.4 containing 100 μg/ml catalase) was incubated with the substrate (0 to 80 mM of N-formyl-Met-Ala, Sigma, USA) at 30° C. for 30 min. The reaction was terminated by addition of 50 μl of 4% $HClO_4$ and further incubated (37° C. for 2 h) with TNBSA reagent (0.01% in 0.1M $NaHCO_3$ buffer, pH 8.4). Following addition of 10% SDS (250 μl) and 1N HCl (125 μl), the highly chromogenic derivative generated due to reaction of primary amine with TNBSA was measured at 335 nm (Hermanson G, Bioconjugate techniques, Academic press, San Diego, Calif., 1996, pp, 112-113). The values obtained were corrected by subtracting the blank (all ingredients except mPDF enzyme) readings. Standard curves were prepared with known amounts (0-42.8 nmoles) of methionine. The determination of the catalytic parameters from three independent experiments using N-formyl-methionine-alanine as the substrate indicated that mPDF is an active enzyme with Michalis-Menton constant ($K_m$) of 4.1±0.2 mM, velocity maxima ($V_{max}$) of 13.3±0.7 µmoles/min/mg protein and catalytic efficiency ( ) of 1220±6 $M^{-1}s^{-1}$.

Mycobacterial peptide deformylase enzyme activity was highly stable and resistant to oxidizing agent like hydrogen peroxide:

The enzyme activity of the recombinant protein (maintained at a concentration of 3.5 µg/ml) IN TNBSA assay as mentioned above when monitored as the function of time, exhibited a half-life of 4.1±0.7 h. Thus, despite being $Fe^{+2}$ at its metal binding core, the recombinant mPDF found to be very stable compared to that of E. coli. This observation together with the fact that M. tuberculosis has to cope up with oxidative stress for its survival within the host, led us to monitor the effect of oxidizing agent, like $H_2O_2$ (hydrogen peroxide), on the deformylating ability of mPDF. While micromolar concentration has been reported to cause rapid and complete inactivation of E. coli enzyme (Rajagopalan and. Pei, J. Biol. Chem. 273 22305-22310 1998), we found pre-incubation (up to 2 h at 30° C. with 70 ng protein/reaction) with 500 mM of $H_2O_2$, did not show any significant effect on the deformylating ability of mPDF compared to the untreated control. Thus, our results established that despite the commonality with other bacterial homologues, mPDF certainly maintained distinction in its behavior.

Figure 5:
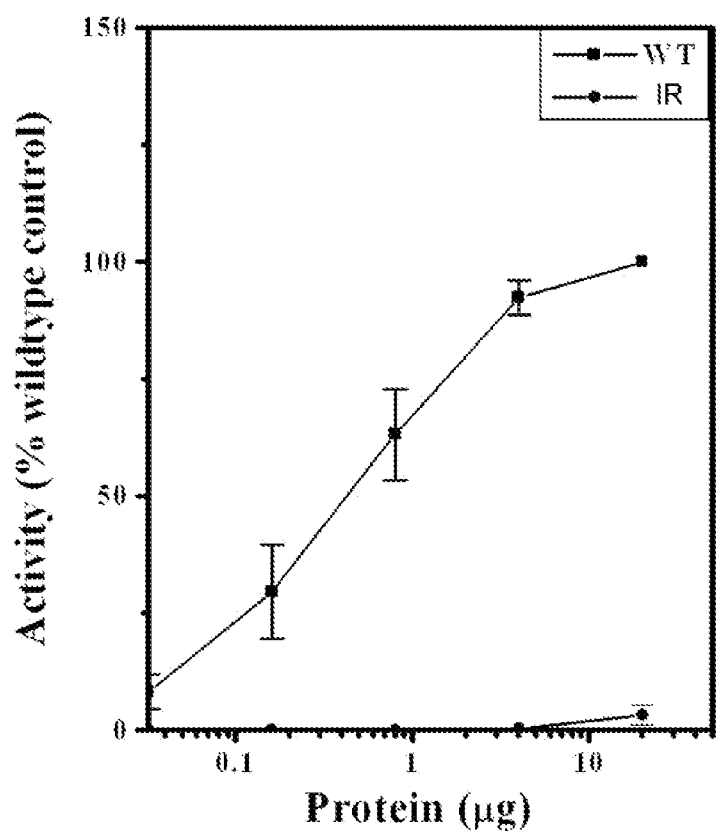
FIG. 5 is a schematic representation of the effect of mutations on the enzyme activity of *M. tuberculosis* peptide deformylase.

Identification of an insertion region in mycobacterial peptide deformylase enzyme that is involved in maintaining enzymatic stability:

Like other gram-positive bacteria (type II class), mPDF possessed insertions (amino acid residues 74-85; IR in FIG. 1), between conserved motifs I and II. We created deletion mutants of mPDF, at the insertion sequences (designated as IR where twelve amino acids "MTARRRGVVINP" (SEQ ID NO: 26) were deleted) employing PCR based mutagenesis approach (Shirley, K., et al., PCR Primer: A Laboratory Manual pp 143-155 in C. W. Dieffenbach, G. S. Dveksler, (ed.). Cold Spring HarborLaboratory, Cold Spring Harbor, N.Y. 1995). This was followed by assessment of the enzyme activity to evaluate contribution of these regions on the deformylation ability of mPDF. The enzyme activity of mPDF was determined in the presence of catalase and BSA using N-formyl-Met-Ala as the substrate in TNBSA assay as mentioned above. The expressed mutant proteins (IR) were recognized by the anti-his tag antibody as evidenced by the Western blotting. On use of even excess amount of protein (20 µg incubated with 5 mM of N-formyl-Met-Ala) in assays, IR mutant hardly showed any deformylase activity (FIG. 5).

Antisense oligonucleotide against insertion region inhibits mycobacterial growth in culture and peptide deformylase enzyme production:

Essentiality of def genes in many pathogenic bacteria led to its use as a promising drug target (Yuan et al., *Drug Discov Today* 6, 954-961(2001). It has also been reported that cultures incubated with inhibitors of this enzyme affect the growth of the bacteria (Clements, et al., *Antimicrob, Agents. Chemother* 45, 563-570 2001 and Cynamon, et al., *J. Antimicrob. Chemother* 53, 403-405 2004). Since insertion sequences are crucial for maintaining the enzymatic activity of mPDF, we further examined the contribution of this region on the growth profile of *Mycobacterium smegmatis* strain $mc^2155$, a fast growing saprophyte which has often been used as a model for genetic studies of M. tuberculosis (Flint, et al., *Proc. Natl. Acad. Sci. U.S.A.* 101, 12598-12603 2004). For this purpose, the bacterial culture was grown in the presence of 5' phosphothiorate modified antisense oligodeoxyribonucleotide, PS-ODN1, designed to span the region (bases 219-249 of M. tuberculosis def) mostly conserved in all mycobacterial species (~73% homology at the nucleotide level between defs of M. tuberculosis and M. smegmatis).

Figures 6A, 6B:
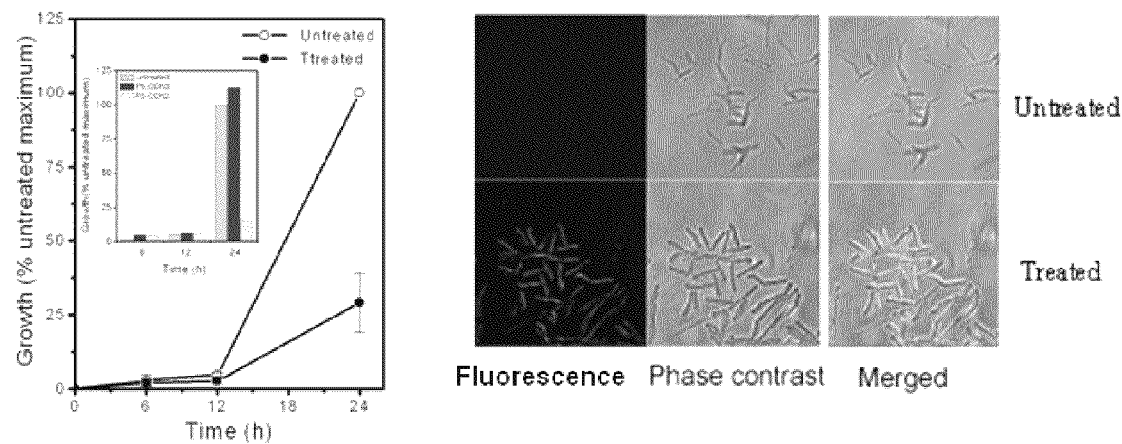
FIGS. 6A and 6B represent an effect of antisense oligonucleotides of conserved insertion region of mycobacterial peptide deformylase on growth.
Figure 7:
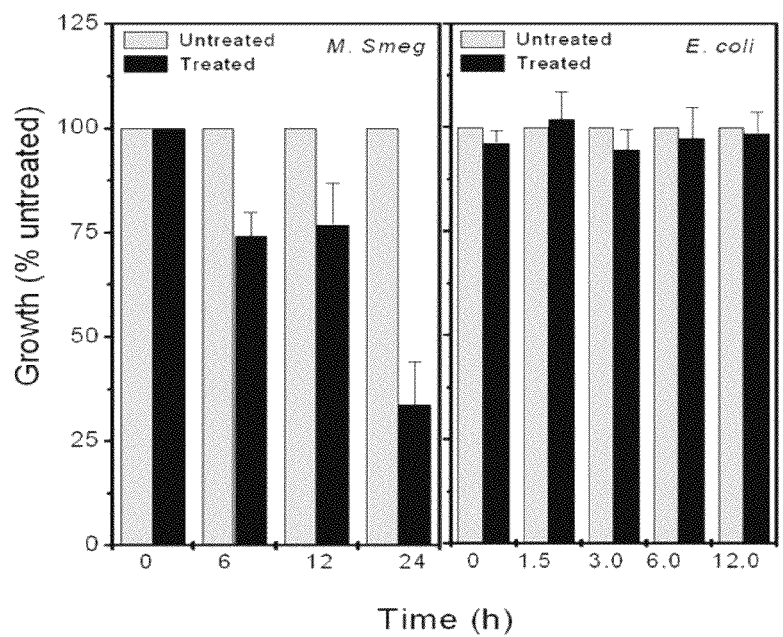
FIG. 7 depicts different bacterial growth in response to antisense oligonucleotides of conserved insertion region of mycobacterial peptide deformylase.

Growth profile of the bacterium was monitored at different time intervals (0-24 h) by recording the absorbance at 600 nm as well as by counting colony forming units. Compared to the untreated culture, our results showed a five-fold decrease in growth of M. smegmatis at 24 h when treated with PS-ODN1 (FIGS. 6A and 7, left panel). This finding was confirmed by using another antisense oligodeoxyribonucleotide (PS-ODN2) within this region (spanning bases 229-255 of M. tuberculosis def, 86% homology at the nucleotide sequences between M. tuberculosis and M. smegmatis) where all bases had phosphothiorate modification (inset of FIG. 6A). We did not observe such growth inhibition when the bacterial culture was treated with a non-specific 5' phosphothiorate modified antisense oligodeoxyribonucleotide, PS-ODN3, designed based on non-homologous sequences (22% homology between bases 100-117 of def of M. tuberculosis and M. smegmatis). Since PS-ODN1 was mycobacteria specific (insertion sequences were absent in other bacteria), it had no effect on growth profile of E. coil (FIG. 7, right panel).

To ensure that PS-ODN1 permeabilized within the M. smegmatis cells, it was conjugated with flourescein at the 3'-end (PS-ODN4) and following treatment for 24 h, when visualized in a confocal microscope, exhibited fluorescence (FIG. 6B). Thus, all these lines of evidence establish that PS-ODNs targeted against the insertion region typical of mycobacterial species, permeabilized inside the cell and specifically inhibited the growth of M. smegmatis.

Figure 8:
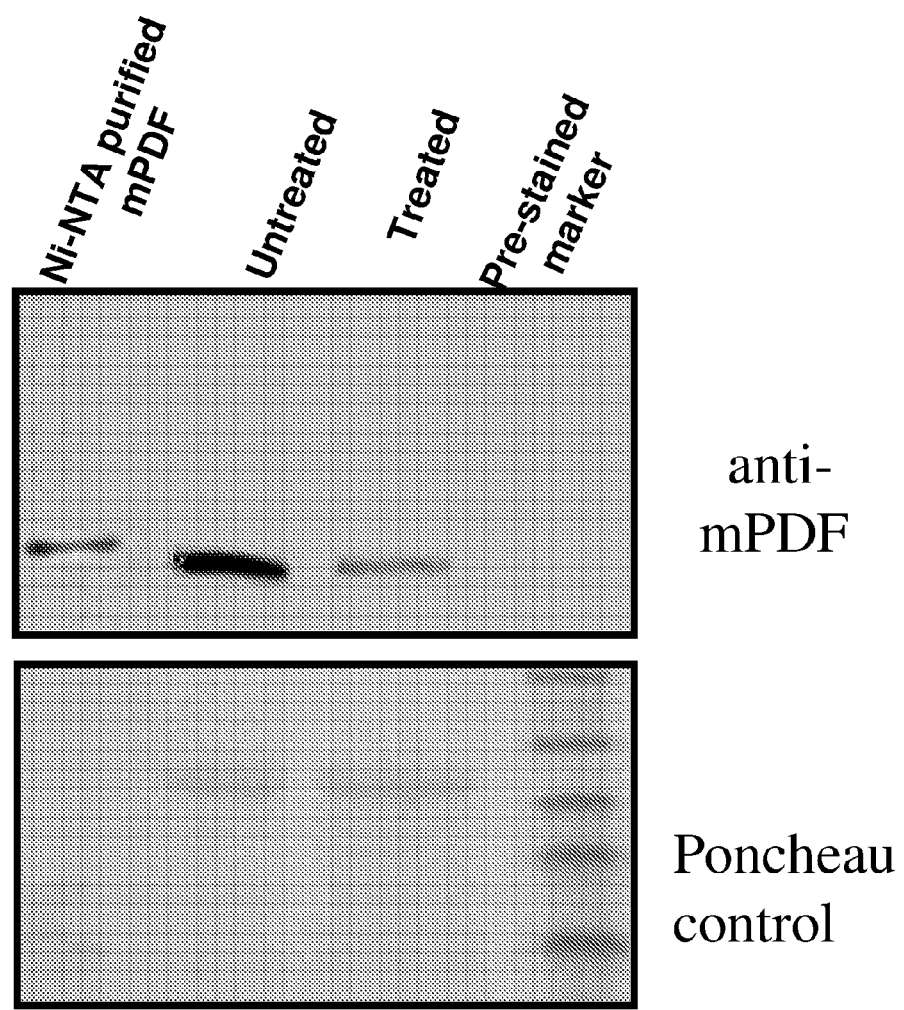
FIG. 8 depicts the expression of peptide deformylase protein in response to antisense oligonucleotide treatment.

To determine whether PS-ODNs inhibit expression of the native PDF protein in M. smegmatis, cultures were grown either in presence or absence of PS-ODN1 for 24 h. Following pelleting of cultures, the soluble fractions of both treated and untreated cell, lysates were prepared in 20 mM phosphate buffer (pH 7.4). These samples were then subjected to SDS-PAGE (amount of protein loaded=50 µg per slot) and Western blotting using polyclonal antibody against recombinant mPDF. Compared to the untreated control (see Ponceau S stained blot which served as a loading control, FIG. 8, upper panel), significant reduction in the level of expression of endogenous PDF protein was noticed in M. smegmatis cells treated with PS-ODN1 (FIG. 8, lower panel). Taken together our results establish that the insertion region plays a pivotal role towards the functionality of this enzyme.

The following examples are given by way of illustration of the present invention and therefore should not be construed to limit the scope of the present invention.

EXAMPLES

Example 1

Nucleotide derived amino acid sequence of mPDF was compared with 'nr' database in BLAST-P programme using mail server at NIH (Altschul et al., Nucleic. Acids. Res. 25 3389-3402 1997). The multiple sequence alignments of the retrieved sequences were carried out using the Clustal X 1.81 program (Thompson et al., Nucleic. Acids. Res. 25: 4876-4882 1997.). Analyses of amino acid sequences of all eubacterial PDFs revealed the presence of three (I: GXGXAAXQ (SEQ ID NO: 27), II: EGCLS (SEQ ID NO: 28) and III: QHEXXH (SEQ ID NO: 29) where X is any hydrophobic residue) highly conserved motifs (FIG. 1), despite their broad categorization in the literature as type I (gram-negative) and type II (gram-positive) classes. We compared nucleotide derived amino acid sequence of mPDF with well-characterized representatives belonging to both type I (*E. coli*) and type II (*Staphylococcus aureus*) classes. Analysis of *M. tuberculosis* peptide deformylase sequence revealed that the mPDF possesses an insertion (amino acid residues 74-85; denoted as IR in FIG. 1). This was followed by alignment of PDF sequences of different mycobacterial species. When compared between different mycobacterial species, the insertion region of *M. tuberculosis* peptide deformylase exhibits ~84% identity (FIG. 2).

Sequence alignment of *M. tuberculosis* enzyme with that of other bacterial iron-containing peptide deormylases:

Referring to FIG. 1, nucleotide derived amino acid sequences of iron-containing peptide deformylase from *E. coli*, *Staphylococcus aureus* and *M. tuberculosis* were aligned using the Clustal X 1.84 programme. Asterix and dots are used to denote identical and similar amino acids respectively. Amino acids constituting insertion region (74-85) deleted to create ΔIR mutant are underlined.

Multiple sequence alignment of peptide deformylase enzyme from different mycobacterial species:

Referring to FIG. 2, mycobacterial sequences retrieved through PSI-BLAST were aligned by Clustal X 1.84 programme. Insertion region specific to mycobacterial deformylase containing conserved residues is underlined. Asterix and dots are used to denote identical and similar amino acids respectively.

Example 2

The def open reading frame (594 bp) was PCR amplified at annealing temperature of 50° C. using Genomic DNA from *M. tuberculosis*. Primers (CR1: 5' CATATGGCAGTGG-TACCC 3' SEQ ID NO: 15 where NdeI site was incorporated and CR3: 5' CCATTAGTGACCGAACGGG 3' SEQ ID NO: 16) used were designed based on def (Rv0429c) sequence of published *M. tuberculosis* genome (Cole et al., Nature. 393 537-544 1998). The PCR was carried out using Expand long template PCR system (Roche) following manufacturer's recommended protocol.

Following treatment with DNA polymerase I (Klenow), the PCR-amplified fragment was initially cloned at SmaI site of pUC19 vector (pUC-mPDF) following standard protocols (Sambrook, J. and Russel, D. *Molecular cloning: a Laboratory Manual*. Cold Spring Harbor Laboratory Press, Cold spring Harbor, N.Y., USA 2001) and its nucleic acid sequence was determined using an automated sequencer (Applied Biosystems). Sequencing of this fragment following cloning in pUC19 indicated 100% identity at the nucleotide level with the published def sequence of *M. tuberculosis* (Cole et al., Nature. 393 537-544 1998).

In order to characterize the enzymatic properties of mPDF, 594 bp fragment containing the def open reading frame was excised out by restriction digestion of pUC-mPDF with NdeI/HindIII restriction enzymes and ligated to the corresponding sites of pET28c following standard procedures (Sambrook, J. and Russel, D. *Molecular cloning: a Laboratory Manual*. Cold Spring Harbor Laboratory Press, Cold spring Harbor, N.Y., USA 2001). This resulted in a construct designated as pET-mPDF (FIG. 3), which was transformed in *E. coli* strain BL21(DE3) to obtain recombinant protein. SDS-PAGE analysis of the cell lysate prepared from host cells harboring plasmid pET-mPDF indicated over-expression of a ~30 kDa protein following IPTG induction (FIG. 4, left panel, compare lanes 2 and 3).

The over-expressed protein was found in the pellet fraction (FIG. 4, left panel, compare lanes 4 and 5), it was solubilized with 3 M urea (FIG. 4, left panel, lane 6) and dialyzed against 20 mM phosphate buffer. Subsequent affinity purification of the soluble protein (FIG. 4, left panel, lane 8) on Ni-NTA column revealed the molecular mass of 31±1.4 kDa (Mean±SD, n=7). The expressed protein had an additional 19 amino acids (HHHHHHSSGLVPRGSH (SEQ ID NO: 30)) at the amino-terminal end from the vector including that of a poly histidine region (six residues). The amino-terminal extension not only facilitated the affinity purification of the protein but also provided the means of detection of mPDF protein in Western blot using anti-his tag monoclonal antibody (FIG. 4, right panel, lanes 2 and 3). This construct was designated as the wild-type in our studies.

Schematic representation of cloning of mycobacterial peptide deformylase gene in expression vector:

Referring to FIG. 3, the def open reading frame (594 bp) was PCR amplified using Genomic DNA from *M. tuberculosis*. Following treatment with DNA polymerase I (Klenow), the PCR-amplified fragment was cloned in SmaI site of pUC19 vector (pUC-PDF) and its nucleic acid sequence was confirmed by restriction digestion followed by nucleic acid sequencing. The construct was subsequently used for subcloning of the open reading frame at NdeI/HindIII sites of pET28c and transformed in *E. coil* strain DH5α to obtain pET-PDF (WT). PCR amplified products containing mutation at the desired sites were digested with unique SacII/HindIII and incorporated at the corresponding site in pET-PDF construct.

Purification of peptide deformylase of *M. tuberculosis* expressed in *E. coli.:*

Referring to FIG. 4, overnight cultures of BL21(DE3) cells harbouring pET-PDF or deletion mutant (IR) were processed as described in the text. Protein samples at various stages of purification were subjected to 12% SDS-PAGE followed by Coomassie Brilliant Blue staining (left panel) and Western blotting using anti-histidine antibody (right panel). Left panel: Lane 1, molecular weight marker; lane 2, crude extract of cells transformed with pET-PDF; lane 3, crude extract of cells transformed with pET-PDF following IPTG induction; lane 4, low speed supernatant fraction; lane 5, pellet fraction obtained after low speed centrifugation; lane 6, urea solubilized supernatant fraction; lane 7, urea solubilized pellet fraction after low speed centrifugation; lane 8, Ni-NTA resin purified protein. Right panel: Lane 1, crude extract of cells transformed with pET-PDF; lane 2, crude extract of cells transformed with pET-PDF following IPTG induction; lane 3, Ni-NTA resin purified protein. The arrow heads indicate the position of purified mPDF. Numbers denote the size of the molecular mass of the marker proteins.

To establish importance of the insertion region 74 to 85, we constructed a mutant deleting amino acid residues 74-85 of *M. tuberculosis* peptide deformylase using PCR-based approaches. The mutant was generated using pUC-PDF as the template following PCR-based methods (Shirley, K., et al., PCR Primer: A Laboratory Manual pp 143-155 in C. W. Dieffenbach, G. S. Dveksler, (ed.). Cold Spring HarborLaboratory, Cold Spring Harbor, N.Y. 1995). The PCR was carried out with two external (primers CR26: 5' GGAATTC-CATATGGCAGTCGTACCC3' SEQ ID NO: 17 and CR27: 5'CCCAA GCTT TTAGTGACCGAACGG3' SEQ ID NO: 18) and two internal primers (CR88: 5'GCGGACCGCGCA GTG CTTGAGACCTC 3' SEQ ID NO: 19 and CR87: 5'GAGGTCTCAAGCACTGCGCGGTCCG 3' SEQ ID NO: 20 designed eliminating 36 base-pairs corresponding to amino acids residue 74-85). To generate desired mutation two sets of primary PCR reactions (using PCR primers CR27/CR87 and CR26/CR88 and pUC-PDF as the template) were carried out. The PCR amplified product obtained in primary reactions was mixed at the ratio of 1:1. Following mixing, the PCR product was used as template to carry out secondary PCR with external primer (CR26/CR27). The final PCR product containing desired mutation was purified in 0.8% agarose gel and digested with SacII/HindIII and incorporated in the corresponding sites of pET-mPDF (FIG. 3). The mutant construct obtained in this way was designated as pET-ΔIR PDF. This (mutant construct) was expressed and purified similarly as mentioned for the wild type. This was followed by monitoring of enzyme activities of wild-type and mutant proteins.

The ability of mPDF or mutant protein to deformylate methionine was assessed in a spectrophotometric assay following the method described elsewhere (Hermanson G, Bioconjugate techniques, Academic press, San Diego, Calif., 1996, pp, 112-113) with slight modification. Briefly, in 50 μl reaction volume mPDF or mutant protein (usually 32 ng-20 μg) in 1× assay buffer (100 mM phosphate buffer, pH 7.4 containing 100 μg/ml catalase) was incubated with the substrate (5 mM of N-formyl-Met-Ala, Sigma, USA) at 30° C. for 30 min. The reaction was terminated by addition of 50 μl of 4% $HClO_4$ and further incubated (37° C. for 2 h) with Tri nitrobenzenesulphonic acid (TNBSA) reagent (0.01% in 0.1M $NaHCO_3$ buffer, pH 8.4). Following addition of 10% SDS (250 μl) and 1N HCl (125 μl), the highly chromogenic derivative generated due to reaction of primary amine with TNBSA was measured at 335 nm. The values obtained were corrected by subtracting the blank (all ingredients except enzyme) readings. Standard curves were prepared with known amounts (0-42.8 nmoles) of methionine and the enzyme activity of mPDF was expressed as nmoles of free amino group produced/min/mg protein. Finally, the data presented in the form of Mean±SD from at least three independent experiments. The deletion of the entire insertion region (ΔIR mutant spanning residues 74-85) completely abolished the enzyme activity when monitored as a function of protein concentrations (FIG. 5). Thus, this result indicated the importance of the insertion region towards the enzyme activity of M. tuberculosis peptide deformylase.

Effect of mutations on the enzyme activity of M. tuberculosis peptide deformylase.

Referring to FIG. 5, deletion mutant (ΔIR 74-85) was created using PCR based mutagenesis method as described in text. Following expression, wild type and mPDF mutant proteins were purified. The deformylation ability of mutant ΔIR (74-85) and wild type (WT) were compared as a function of increasing protein concentrations (0.032, 0.16, 0.8, 4.0, 0.20 μg) using 5 mM N-formyl-Met-Ala as substrate.

Example 3

We further examined the contribution of this region on the growth profile of *Mycobacterium smegmatis* strain mc$^2$155, a fast growing saprophyte which has often been used as a model for genetic studies of M. tuberculosis (Flint, et al., *Proc. Natl. Acad. Sci. U.S.A.* 101, 12598-12603 2004). ~1×10$^5$ cells of M. smegmatis (obtained from confluent culture and cell number adjusted by serial dilution) were incubated with 10 μM PS-ODN1 in 3 ml broth (7H9 Middlebrook media supplemented with 10% ADC). The PS-ODN1 was designed to span the region (bases 219-249 of M. tuberculosis def) mostly conserved in all mycobacterial species (~73% homology at the nucleotide level between clefs of M. tuberculosis and M. smegmatis). Small aliquots were removed at different time intervals (0, 6, 12, 24 hr) and optical density at 600 nm was recorded to obtain a growth profile of bacterial cultures for treated and untreated with PS-ODN1. Simultaneously, the bacterial cells withdrawn at different time intervals were washed, plated on 7H10 Middlebrook agar (supplemented with 10% ADC) following serial dilution and enumerated for colony forming units after incubation for 3 days at 37° C. Compared to the untreated culture, our results showed a fivefold decrease (FIGS. 6A and 7) in growth of M. smegmatis cultures grown in the presence of PS-ODN1 (similar growth profiles were obtained when growth monitored by determining optical density of the culture at 600 nm and by counting the number of colonies obtained on plates). This finding was confirmed by using another antisense oligodeoxyribonucleotide (PS-ODN2) within this region (spanning bases 229-255 of M. tuberculosis def, 86% homology at the nucleotide sequences between M. tuberculosis and M. smegmatis) where all bases had phosphothiorate modification (inset of FIG. 6A).

Further, to ensure that PS-ODN1 permeabilized within the M. smegmatis cells, PS-ODN1 were conjugated with 3'Flourescein label and used for the treatment of mycobacterial culture (~1×10$^5$ cells of M. smegmatis were incubated with 10 μM PS-ODNs in 3 ml 7H9 Middlebrook broth supplemented with 10% ADC and grown at 37° C./200 rpm for 24 hrs). At the end of the experiment, following washing with 1×PBS (pH7.4) when cells treated with PS-ODN1 conjugated with 3'Flourescein were visualized in a confocal microscope exhibited fluorescence (FIG. 6B). Since PS-ODN1 was mycobacteria specific, in E. coli where this insertion sequence is absent, when culture was treated with 10 μM PS-ODN1 had no effect on its growth. (FIG. 7, right panel). Thus, all these lines of evidence establish that PS-ODNs targeted against the insertion region typical of mycobacterial species, permeabilized inside the cell and specifically inhibited the growth of M. smegmatis.

Effect of antisense oligonucleotides of conserved insertion region of mycobacterial peptide deformylase on growth.

Referring to FIGS. 6A-6B, M. smegmatis culture (1×10$^5$ cells in 3 ml Middlebrook 7H9 medium supplemented with 10% cocktail of albumin, dextrose and catalase) were incubated with PS-ODNs (10 μM) designed against insertion region typical to mycobacterial species. Aliquots were removed at different time intervals (0, 6, 12, 24 hr) and optical density at 600 nm was recorded to obtain a growth profile of bacterial cultures treated and untreated with PS-ODNs. Inset: Mycobacterial culture when treated with a non-specific 5' phosphothiorate modified antisense oligodeoxyribonucleotide, PS-ODN3, designed based on non-homologous sequences (22% homology between bases 100-117 of def of M. tuberculosis and M. smegmatis) and grown as described above, we did not observe such growth inhibition (B) Bacterial cells treated with 3'Flourescein conjugated PS-ODN for 24 h were visualized under confocal microscope. Upper panel: untreated M. smegmatis cells, lower panel: M. smegmatis treated with 3'Flourescein conjugated PS-ODN.

Different bacterial growth in response to antisense oligonucleotides of conserved insertion region of mycobacterial peptide deformylase.

Referring to FIG. 7, bacterial cultures grown (1×10$^5$ cells in 3 ml Middlebrook 7H9 medium supplemented with 10% cocktail of albumin, dextrose and catalase for M. smegmatis and Lauria-Bertani medium for E. coli) in absence and presence of 10 μM PS-ODNs (designed against insertion region specific to mycobacterial species) removed at different time intervals were washed and plated on Middlebrook 7H10-Agar supplemented with 10% cocktail of albumin, dextrose and catalase (M. smegmatis) or Lauria-Bertani-Agar (E. coli)

plates following serial dilution. Colonies obtained after incubation for 3 days (*M. Smegmatis*) and 12 hrs (*E. coli*) at 37° C. were enumerated and plotted as a percent growth of untreated cultures.

Example 4

To determine whether PS-ODNs inhibit expression of the native PDF protein in *M. smegmatis*, cultures were grown either in presence or absence of PS-ODN1 for 24 h. Following pelleting of cultures, the soluble fractions of both treated and untreated cell, lysates were prepared in 20 mM phosphate buffer (pH 7.4). These samples were then subjected to SDS-PAGE (amount of protein loaded=50 μg per slot) and Western blotting using polyclonal antibody against recombinant mPDF. Compared to the untreated control (see Ponceau S stained blot which served as a loading control, FIG. 8, upper panel), significant reduction in the level of expression of endogenous PDF protein was noticed in *M. smegmatis* cells treated with PS-ODN1 (FIG. 8, lower panel). Taken together our results establish that the insertion region plays a pivotal role towards the functionality of this enzyme.

Expression of peptide deformylase protein in response to antisense oligonucleotide treatment.

Referring to FIG. 8, *M. smegmatis* culture ($1\times10^5$ cells in 3 ml Middlebrook 7H9 medium supplemented with 10% cocktail of albumin, dextrose and catalase) were incubated with PS-ODNs (10 μM) designed against insertion region typical to mycobacterial species for 24 h. Cells were harvested, sonicated and supernatant fraction (13200 rpm) following protein estimation was used subsequently. Proteins resolved at 12% SDS-PAGE (loaded 50 μg protein per slot for treated or untreated samples) were subjected to Western blot analysis using polyclonal antibodies raised against recombinant purified mPDF. Upper panel: Blot probed with polyclonal antibody against mPDF, Lane 1; Ni-NTA purified mPDF (as control), Lane 2, supernatant fraction from untreated *M. smegmatis*, Lane 3, supernatant fraction from *M. smegmatis* treated with 10 μM PS-ODNs, Lane 4, Prestained protein molecular weight marker.

What is claimed is:

1. An antisense oligonucleotide fully complementary to a polynucleotide sequence encoding a mycobacterial deformylase peptide insertion sequence XTXRRRGVVINP (SEQ ID NO: 13), wherein X can be any naturally occurring amino acid, or a peptide insertion sequence 90% to 95% similar to the corresponding peptide insertion sequence from M. tuberculosis, M. smegmatis, M. bovis, M. avium, or M. leprae, and wherein the antisense oligonucleotide is modified with phosphorothioates.

2. The antisense oligonucleotide of claim 1, wherein the antisense oligonucleotide is fully complementary to SEQ ID NO: 21.

3. The antisense oligonucleotide of claim 1, wherein the oligonucleotide is a phosphorothioate modified oligodeoxynucleotide.

4. A method for inhibiting the activity and growth of mycobacteria the method comprising a step of administering an antisense oligonucleotide fully complementary to a polynucleotide sequence encoding a mycobacterial deformylase peptide insertion sequence XTXRRRGVVINP (SEQ ID NO: 13), wherein X can be any naturally occurring amino acid, or a peptide insertion sequence 90% to 95% similar to the corresponding peptide insertion sequence from M. tuberculosis, M. smegmatis, M. bovis, M. avium, or M. leprae.

5. The antisense oligonucleotide of claim 1, wherein the antisense oligonucleotide inhibits the production of a mycobacterial peptide deformylase enzyme.

6. The antisense oligonucleotide of claim 1, wherein the oligonucleotide is used against mycobacteria.

7. A composition comprising the antisense oligonucleotide of claim 1.

8. The composition according to claim 7, further comprising a pharmaceutically acceptable carrier, additive, or diluent.

9. The antisense oligonucleotide of claim 1, wherein the phosphorothioate modified antisense oligonucleotide consists of the oligonucleotide sequence of SEQ ID NO:14.

10. The method according to claim 4, further comprising modifying the antisense oligonucleotide with phosphorothioates.

11. The method according to claim 4, wherein inhibiting the activity and growth of mycobacteria comprises inhibiting the production of mycobacterial peptide deformylase enzyme.

12. The method according to claim 4, wherein administering the antisense oligonucleotide comprises administering an antisense oligonucleotide complementary to the oligonucleotide sequence of SEQ ID NO:21.

13. The method according to claim 4, wherein administering the antisense oligonucleotide comprises administering the oligonucleotide of SEQ ID NO:14.

14. The method according to claim 4, wherein the antisense oligonucleotide is a drug used against mycobacteria and the method further comprises administering a pharmaceutically acceptable carrier, additive, or diluent.

15. The method according to claim 4, wherein the antisense oligonucleotide is a composition comprising a pharmaceutically acceptable carrier, additive, or diluent.

16. A composition comprising an isolated and phosphorothioated antisense oligonucleotide fully complementary to a polynucleotide sequence encoding a mycobacterial deformylase peptide insertion sequence XTXRRRGVVINP (SEQ ID NO: 13), wherein X can be any naturally occurring amino acid, or a peptide insertion sequence 90% to 95% similar to the corresponding peptide insertion sequence from *M. tuberculosis, M. smegmatis, M. bovis, M. avium*, or *M. leprae*.

17. The composition according to claim 15, further comprising a pharmaceutically acceptable carrier, additive, or diluent.

18. The composition according to claim 15, wherein the isolated and phosphorotioated antisense oligonucleotide comprises the oligonucleotide sequence of SEQ ID NO:14.

* * * * *

SEQUENCE LISTING

```
<160> NUMBER OF SEQ ID NOS: 21

<210> SEQ ID NO 1
<211> LENGTH: 162
<212> TYPE: PRT
<213> ORGANISM: Staphylococcus aureus

<400> SEQUENCE: 1

Met Ala Ile Lys Lys Leu Val Pro Ala Ser His Pro Ile Leu Thr Lys
1               5                   10                  15

Lys Ala Gln Ala Val Lys Thr Phe Asp Asp Ser Leu Lys Arg Leu Leu
            20                  25                  30

Gln Asp Leu Glu Asp Thr Met Tyr Ala Gln Glu Ala Ala Gly Leu Cys
        35                  40                  45

Ala Pro Gln Ile Asn Gln Ser Leu Gln Val Ala Ile Ile Asp Met Glu
    50                  55                  60

Met Glu Gly Leu Leu Gln Leu Val Asn Pro Lys Ile Ile Ser Gln Ser
65                  70                  75                  80

Asn Glu Thr Ile Thr Asp Leu Glu Gly Ser Ile Thr Leu Pro Asp Val
                85                  90                  95

Tyr Gly Glu Val Thr Arg Ser Lys Met Ile Val Val Glu Ser Tyr Asp
            100                 105                 110

Val Asn Gly Asn Lys Val Glu Leu Thr Ala His Glu Asp Val Ala Arg
        115                 120                 125

Met Ile Leu His Ile Ile Asp Gln Met Asn Gly Ile Pro Phe Thr Glu
    130                 135                 140

Arg Ala Asp Arg Ile Leu Thr Asp Lys Glu Val Glu Ala Tyr Phe Ile
145                 150                 155                 160

Asn Asp

<210> SEQ ID NO 2
<211> LENGTH: 203
<212> TYPE: PRT
<213> ORGANISM: Streptococcus pneumoniae

<400> SEQUENCE: 2

Met Ser Ala Ile Glu Arg Ile Thr Lys Ala Ala His Leu Ile Asp Met
1               5                   10                  15
```

```
Asn Asp Ile Ile Arg Glu Gly Asn Pro Thr Leu Arg Thr Val Ala Glu
                20                  25                  30

Glu Val Thr Phe Pro Leu Ser Asp Gln Glu Ile Ile Leu Gly Glu Lys
            35                  40                  45

Met Met Gln Phe Leu Lys His Ser Gln Asp Pro Val Met Ala Glu Lys
 50                  55                  60

Met Gly Leu Arg Gly Val Gly Leu Ala Ala Pro Gln Leu Asp Ile
 65                  70                  75                  80

Ser Lys Arg Ile Ile Ala Val Leu Val Pro Asn Ile Val Glu Glu Gly
                85                  90                  95

Glu Thr Pro Gln Glu Ala Tyr Asp Leu Glu Ala Ile Met Tyr Asn Pro
                100                 105                 110

Lys Ile Val Ser His Ser Val Gln Asp Ala Ala Leu Gly Glu Gly Glu
                115                 120                 125

Gly Cys Leu Ser Val Asp Arg Asn Val Pro Gly Tyr Val Val Arg His
    130                 135                 140

Ala Arg Val Thr Val Asp Tyr Phe Asp Lys Asp Gly Glu Lys His Arg
145                 150                 155                 160

Ile Lys Leu Lys Gly Tyr Asn Ser Ile Val Val Gln His Glu Ile Asp
                165                 170                 175

His Ile Asn Gly Ile Met Phe Tyr Asp Arg Ile Asn Glu Lys Asp Pro
                180                 185                 190

Phe Ala Val Lys Asp Gly Leu Leu Ile Leu Glu
                195                 200

<210> SEQ ID NO 3
<211> LENGTH: 169
<212> TYPE: PRT
<213> ORGANISM: Haemophilus influenzae

<400> SEQUENCE: 3

Met Thr Ala Leu Asn Val Leu Ile Tyr Pro Asp Asp His Leu Lys Val
 1               5                  10                  15

Val Cys Glu Pro Val Thr Lys Val Asn Asp Ala Ile Arg Lys Ile Val
                20                  25                  30

Asp Asp Met Phe Asp Thr Met Tyr Gln Glu Lys Gly Ile Gly Leu Ala
                35                  40                  45

Ala Pro Gln Val Asp Ile Leu Gln Arg Ile Ile Thr Ile Asp Val Glu
        50                  55                  60

Gly Asp Lys Gln Asn Gln Phe Val Leu Ile Asn Pro Glu Ile Leu Ala
 65                  70                  75                  80

Ser Glu Gly Glu Thr Gly Ile Glu Glu Gly Cys Leu Ser Ile Pro Gly
                85                  90                  95

Phe Arg Ala Leu Val Pro Arg Lys Glu Lys Val Thr Val Arg Ala Leu
            100                 105                 110

Asp Arg Asp Gly Lys Glu Phe Thr Leu Asp Ala Asp Gly Leu Leu Ala
        115                 120                 125

Ile Cys Ile Gln His Glu Ile Asp His Leu Asn Gly Ile Leu Phe Val
    130                 135                 140

Asp Tyr Leu Ser Pro Leu Lys Arg Gln Arg Ile Lys Glu Lys Leu Ile
145                 150                 155                 160

Lys Tyr Lys Lys Gln Ile Ala Lys Ser
                165

<210> SEQ ID NO 4
```

```
<211> LENGTH: 178
<212> TYPE: PRT
<213> ORGANISM: Leptospira interrogans

<400> SEQUENCE: 4
```

Met Ser Val Arg Lys Ile Leu Arg Met Gly Asp Pro Ile Leu Arg Lys
1               5                   10                  15

Ile Ser Glu Pro Val Thr Glu Asp Glu Ile Gln Thr Lys Glu Phe Lys
                20                  25                  30

Lys Leu Ile Arg Asp Met Phe Asp Thr Met Arg His Ala Glu Gly Val
            35                  40                  45

Gly Leu Ala Ala Pro Gln Ile Gly Ile Leu Lys Gln Ile Val Val Val
        50                  55                  60

Gly Ser Glu Asp Asn Glu Arg Tyr Pro Gly Thr Pro Asp Val Pro Glu
65                  70                  75                  80

Arg Ile Ile Leu Asn Pro Val Ile Thr Pro Leu Thr Lys Asp Thr Ser
                85                  90                  95

Gly Phe Trp Glu Gly Cys Leu Ser Val Pro Gly Met Arg Gly Tyr Val
            100                 105                 110

Glu Arg Pro Asn Gln Ile Arg Met Gln Trp Met Asp Glu Lys Gly Asn
        115                 120                 125

Gln Phe Asp Glu Thr Ile Asp Gly Tyr Lys Ala Ile Val Tyr Gln His
    130                 135                 140

Glu Cys Asp His Leu Gln Gly Ile Leu Tyr Val Asp Arg Leu Lys Asp
145                 150                 155                 160

Thr Lys Leu Phe Gly Phe Asn Glu Thr Leu Asp Ser Ser His Asn Val
                165                 170                 175

Leu Asp

```
<210> SEQ ID NO 5
<211> LENGTH: 187
<212> TYPE: PRT
<213> ORGANISM: Enterococcus faecalis

<400> SEQUENCE: 5
```

Met Ile Thr Met Lys Asp Ile Ile Arg Glu Gly Asn Pro Thr Leu Arg
1               5                   10                  15

Ala Val Ala Glu Glu Val Pro Val Pro Ile Thr Glu Glu Asp Arg Gln
                20                  25                  30

Leu Gly Glu Asp Met Leu Thr Phe Leu Lys Asn Ser Gln Asp Pro Val
            35                  40                  45

Lys Ala Glu Glu Leu Gln Leu Arg Gly Gly Val Gly Leu Ala Ala Pro
        50                  55                  60

Gln Leu Asp Ile Ser Lys Arg Ile Ile Ala Val His Val Pro Ser Asn
65                  70                  75                  80

Asp Pro Glu Asn Glu Thr Pro Ser Leu Ser Thr Val Met Tyr Asn Pro
                85                  90                  95

Lys Ile Leu Ser His Ser Val Gln Asp Val Cys Leu Gly Glu Gly Glu
            100                 105                 110

Gly Cys Leu Ser Val Asp Arg Asp Val Pro Gly Tyr Val Val Arg His
        115                 120                 125

Asn Lys Ile Thr Val Ser Tyr Phe Asp Met Ala Gly Glu Lys His Lys
    130                 135                 140

Val Arg Leu Lys Asn Tyr Glu Ala Ile Val Val Gln His Glu Ile Asp
145                 150                 155                 160

```
His Ile Asn Gly Ile Met Phe Tyr Asp His Ile Asn Lys Glu Asn Pro
                165                 170                 175

Phe Ala Leu Lys Glu Gly Val Leu Val Ile Glu
            180                 185

<210> SEQ ID NO 6
<211> LENGTH: 174
<212> TYPE: PRT
<213> ORGANISM: Helicobacter pylori

<400> SEQUENCE: 6

Met Ala Leu Leu Glu Ile Ile His Tyr Pro Ser Lys Ile Leu Arg Thr
1               5                   10                  15

Ile Ser Lys Glu Val Val Ser Phe Asp Ala Lys Leu His Gln Gln Leu
            20                  25                  30

Asp Asp Met Tyr Glu Thr Met Ile Ala Ser Glu Gly Ile Gly Leu Ala
        35                  40                  45

Ala Ile Gln Val Gly Leu Pro Leu Arg Met Leu Ile Ile Asn Leu Pro
    50                  55                  60

Gln Glu Asp Gly Val Gln His Lys Glu Asp Cys Leu Glu Ile Ile Asn
65                  70                  75                  80

Pro Lys Phe Ile Glu Thr Gly Gly Ser Met Tyr Lys Glu Gly Cys
                85                  90                  95

Leu Ser Val Pro Gly Phe Tyr Glu Val Glu Arg Phe Glu Lys Val
                100                 105                 110

Lys Ile Glu Tyr Gln Asn Arg Phe Ala Glu Val Lys Val Leu Glu Ala
            115                 120                 125

Ser Glu Leu Leu Ala Val Ala Ile Gln His Glu Ile Asp His Leu Asn
    130                 135                 140

Gly Val Leu Phe Val Asp Lys Leu Ser Ile Leu Lys Arg Lys Lys Phe
145                 150                 155                 160

Glu Lys Glu Leu Lys Glu Leu Gln Lys Lys Gln Lys His Lys
                165                 170

<210> SEQ ID NO 7
<211> LENGTH: 160
<212> TYPE: PRT
<213> ORGANISM: Bacillus subtilis

<400> SEQUENCE: 7

Met Ala Val Lys Lys Val Val Thr His Pro Ala Glu Val Leu Glu Thr
1               5                   10                  15

Pro Ala Glu Thr Val Thr Val Phe Asp Lys Lys Leu Lys Lys Leu Leu
            20                  25                  30

Asp Asp Met Tyr Asp Thr Met Leu Glu Met Asp Gly Val Gly Leu Ala
        35                  40                  45

Ala Pro Gln Ile Gly Ile Leu Lys Arg Ala Ala Val Val Glu Ile Gly
    50                  55                  60

Asp Asp Arg Gly Arg Ile Asp Leu Val Asn Pro Glu Ile Leu Glu Lys
65                  70                  75                  80

Ser Gly Glu Gln Thr Gly Ile Glu Gly Cys Leu Ser Phe Pro Asn Val
                85                  90                  95

Tyr Gly Asp Val Thr Arg Ala Asp Tyr Val Lys Val Arg Ala Phe Asn
                100                 105                 110

Arg Gln Gly Lys Pro Phe Ile Leu Glu Ala Arg Gly Phe Leu Ala Arg
            115                 120                 125
```

```
Ala Val Gln His Glu Met Asp His Leu Asp Gly Val Leu Phe Thr Ser
        130                 135                 140

Lys Ile Ser Lys Tyr Tyr Thr Glu Asp Glu Leu Ala Asp Met Glu Gly
145                 150                 155                 160

<210> SEQ ID NO 8
<211> LENGTH: 197
<212> TYPE: PRT
<213> ORGANISM: Mycobacterium tuberculosis

<400> SEQUENCE: 8

Met Ala Val Val Pro Ile Arg Ile Val Gly Asp Pro Val Leu His Thr
1               5                   10                  15

Ala Thr Thr Pro Val Thr Val Ala Ala Asp Gly Ser Leu Pro Ala Asp
                20                  25                  30

Leu Ala Gln Leu Ile Ala Thr Met Tyr Asp Thr Met Asp Ala Ala Asn
            35                  40                  45

Gly Val Gly Leu Ala Ala Asn Gln Ile Gly Cys Ser Leu Arg Leu Phe
        50                  55                  60

Val Tyr Asp Cys Ala Ala Asp Arg Ala Met Thr Ala Arg Arg Arg Gly
65                  70                  75                  80

Val Val Ile Asn Pro Val Leu Glu Thr Ser Glu Ile Pro Glu Thr Met
                85                  90                  95

Pro Asp Pro Asp Thr Asp Glu Gly Cys Leu Ser Val Pro Gly Glu
            100                 105                 110

Ser Phe Pro Thr Gly Arg Ala Lys Trp Ala Arg Val Thr Gly Leu Asp
            115                 120                 125

Ala Asp Gly Ser Pro Val Ser Ile Glu Gly Thr Gly Leu Phe Ala Arg
        130                 135                 140

Met Leu Gln His Glu Thr Gly His Leu Asp Gly Phe Leu Tyr Leu Asp
145                 150                 155                 160

Arg Leu Ile Gly Arg Tyr Ala Arg Asn Ala Lys Arg Ala Val Lys Ser
                165                 170                 175

His Gly Trp Gly Val Pro Gly Leu Ser Trp Leu Pro Gly Glu Asp Pro
            180                 185                 190

Asp Pro Phe Gly His
        195

<210> SEQ ID NO 9
<211> LENGTH: 198
<212> TYPE: PRT
<213> ORGANISM: Mycobacterium smegmatis

<400> SEQUENCE: 9

Met Ala Val Val Pro Ile Arg Ile Val Gly Asp Pro Val Leu His Thr
1               5                   10                  15

Pro Thr Glu Pro Val Pro Val Gly Pro Asp Gly Ser Leu Pro Asp Asp
                20                  25                  30

Leu Pro Ala Leu Ile Gln Asp Met Phe Asp Thr Met Asp Ala Ala Asn
            35                  40                  45

Gly Val Gly Leu Ala Ala Asn Gln Ile Gly Val Ala Lys Arg Leu Phe
        50                  55                  60

Val Tyr Asp Cys Ala Pro Thr Arg Gly Gln Thr Thr Arg Arg Arg Gly
65                  70                  75                  80

Val Val Ile Asn Pro Val Leu Glu Thr Ser Glu Val Pro Glu Thr Met
                85                  90                  95
```

```
Pro Asp Pro Asp Glu Asp Glu Glu Gly Cys Leu Ser Val Pro Gly Glu
            100                 105                 110

Asn Phe Pro Thr Gly Arg Ala Asp Trp Ala Arg Val Thr Gly Leu Asp
            115                 120                 125

Ala Asp Gly Ser Pro Ile Thr Leu Glu Gly Glu Asp Leu Phe Ala Arg
            130                 135                 140

Met Leu Gln His Glu Thr Gly His Leu Asp Gly Phe Leu Tyr Leu Asp
145                 150                 155                 160

Arg Leu Val Gly Arg Tyr Ala Arg Ala Ala Lys Lys Ala Val Lys Arg
                165                 170                 175

Asn Gly Trp Gly Gly Val Pro Gly Leu Ser Trp Met Pro Gly Glu Val
            180                 185                 190

Pro Asp Pro Phe Gly His
            195

<210> SEQ ID NO 10
<211> LENGTH: 197
<212> TYPE: PRT
<213> ORGANISM: Mycobacterium bovis

<400> SEQUENCE: 10

Met Thr Val Val Pro Ile Arg Ile Val Gly Asp Pro Val Leu His Thr
1               5                   10                  15

Ala Thr Thr Pro Val Thr Val Ala Ala Asp Gly Ser Leu Pro Ala Asp
                20                  25                  30

Leu Ala Gln Leu Ile Ala Thr Met Tyr Asp Thr Met Asp Ala Ala Asn
            35                  40                  45

Gly Val Gly Leu Ala Ala Asn Gln Ile Gly Cys Ser Leu Arg Leu Phe
    50                  55                  60

Val Tyr Asp Cys Ala Ala Asp Arg Ala Met Thr Ala Arg Arg Arg Gly
65                  70                  75                  80

Val Val Ile Asn Pro Val Leu Glu Thr Ser Glu Ile Pro Glu Thr Met
                85                  90                  95

Pro Asp Pro Asp Thr Asp Asp Glu Gly Cys Leu Ser Val Pro Gly Glu
            100                 105                 110

Ser Phe Pro Thr Gly Arg Ala Lys Trp Ala Arg Val Thr Gly Leu Asp
            115                 120                 125

Ala Asp Gly Ser Pro Val Ser Ile Glu Gly Thr Gly Leu Phe Ala Arg
            130                 135                 140

Met Leu Gln His Glu Thr Gly His Leu Asp Gly Phe Leu Tyr Leu Asp
145                 150                 155                 160

Arg Leu Ile Gly Arg Tyr Ala Arg Asn Ala Lys Arg Ala Val Lys Ser
                165                 170                 175

His Gly Trp Gly Val Pro Gly Leu Ser Trp Leu Pro Gly Glu Asp Pro
            180                 185                 190

Asp Pro Phe Gly His
        195

<210> SEQ ID NO 11
<211> LENGTH: 197
<212> TYPE: PRT
<213> ORGANISM: Mycobacterium avium

<400> SEQUENCE: 11

Met Ala Val Val Pro Ile Arg Ile Val Gly Asp Pro Val Leu His Thr
1               5                   10                  15
```

```
Pro Thr Gln Pro Val Pro Val Gly Asp Asp Gly Ser Leu Pro Ala Asp
            20                  25                  30

Leu Gly Lys Leu Ile Ala Asp Met Tyr Asp Thr Met Asp Ala Ala His
        35                  40                  45

Gly Val Gly Leu Ala Ala Asn Gln Ile Gly Val Gly Leu Arg Val Phe
    50                  55                  60

Val Tyr Asp Cys Ala Asp Asp Arg Gly Leu Thr Glu Arg Arg Arg Gly
65                  70                  75                  80

Val Val Val Asn Pro Val Leu Glu Thr Ser Glu Ile Pro Glu Thr Met
                85                  90                  95

Pro Asp Pro Asp Thr Asp Glu Gly Cys Leu Ser Val Pro Gly Glu
            100                 105                 110

Ser Phe Pro Thr Gly Arg Ala Ser Trp Ala Arg Val Thr Gly Leu Asp
            115                 120                 125

Ala Asp Gly Asn Pro Val Ser Ile Glu Gly His Gly Leu Phe Ala Arg
        130                 135                 140

Met Leu Gln His Glu Thr Gly His Leu Asp Gly Phe Leu Tyr Leu Asp
145                 150                 155                 160

Arg Leu Ile Gly Arg Tyr Ala Arg Ser Ala Lys Arg Ala Val Lys Ser
                165                 170                 175

His Asn Trp Gly Val Pro Gly Leu Ser Trp Met Pro Gly Glu Gly Pro
            180                 185                 190

Asp Pro Phe Gly His
        195

<210> SEQ ID NO 12
<211> LENGTH: 197
<212> TYPE: PRT
<213> ORGANISM: Mycobacterium leprae

<400> SEQUENCE: 12

Met Ala

Asp Pro Phe Gly Pro
        195

<210> SEQ ID NO 13
<211> LENGTH: 12
<212> TYPE: PRT
<213> ORGANISM: Mycobacterium
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Xaa Thr Xaa Arg Arg Arg Gly Val Val Ile Asn Pro
1               5                   10

<210> SEQ ID NO 14
<211> LENGTH: 36
<212> TYPE: DNA
<213> ORGANISM: Mycobacterium tuberculosis

<400> SEQUENCE: 14
cggattgatg accacaccgc gtcggcgggc ggtcat                                36

<210> SEQ ID NO 15
<211> LENGTH: 18
<212> TYPE: DNA
<213> ORGANISM: Artificial
<220> FEATURE:
<223> OTHER INFORMATION: 5'-3' deformylase open reading frame (594bp)
      genomic DNA from M.tuberculosis

<400> SEQUENCE: 15
catatggcag tggtaccc                                                   18

<210> SEQ ID NO 16
<211> LENGTH: 19
<212> TYPE: DNA
<213> ORGANISM: Artificial
<220> FEATURE:
<223> OTHER INFORMATION: 5'-3' deformylase open reading frame (594bp)
      genomic DNA from M.tuberculosis

<400> SEQUENCE: 16
ccattagtga ccgaacgg

```
<223> OTHER INFORMATION: External primer for mutation of deformylase
      protein deleting amino acids 74-85 of M.tuberculosis deformylase
      polypeptide

<400> SEQUENCE: 18
cccaagcttt tagtgaccga acgg                                            24

<210> SEQ ID NO 19
<211> LENGTH: 26
<212> TYPE: DNA
<213> ORGANISM: Artificial
<220> FEATURE:
<223> OTHER INFORMATION: Internal primer for mutation of deformylase
      protein deleting amino acids 74-85 of M.tuberculosis deformylase
      polypeptide

<400> SEQUENCE: 19
gcggaccgcg cagtgcttga gacctc                                          26

<210> SEQ ID NO 20
<211> LENGTH: 25
<212> TYPE: DNA
<213> ORGANISM: Artificial
<220> FEATURE:
<223> OTHER INFORMATION: Internal primer for mutation of deformylase
      protein deleting amino acids 74-85 of M.tuberculosis deformylase
      polypeptide

<400> SEQUENCE: 20
gaggtctcaa gcactgcgcg gtccg                                           25

<210> SEQ ID NO 21
<211> LENGTH: 36
<212> TYPE: DNA
<213> ORGANISM: Artificial
<220> FEATURE:
<223> OTHER INFORMATION: sense oligonucleotide to Mycobacterium
      tuberculosis deformylase gene sequence in SEQ ID NO:14
<220> FEATURE:
<221> NAME/KEY: misc_feature
<222> LOCATION: (1)..(36)
<223> OTHER INFORMATION: 5' - 3' sense oligonucleotide to M.tuberculosis
      deformylase gene sequence as in SEQ ID NO:14

<400> SEQUENCE: 21
atgaccgccc gccgacgcgg tgtggtcatc aatccg                               36
```